United States Patent [19]
Klein et al.

[11] Patent Number: 5,807,862
[45] Date of Patent: Sep. 15, 1998

[54] THERAPEUTIC COMPOUNDS CONTAINING PYRIMIDINYL MOIETIES

[75] Inventors: J. Peter Klein, Vashon; Alistair J. Leigh; Gail E. Underiner, both of Brier; Anil M. Kumar, Seattle, all of Wash.

[73] Assignee: Cell Therapeutics, Inc., Seattle, Wash.

[21] Appl. No.: 478,112

[22] Filed: Jun. 7, 1995

Related U.S. Application Data

[63] Continuation-in-part of Ser. No. 199,368, Feb. 18, 1994, abandoned.

[51] Int. Cl.$^6$ .................... A61K 31/505; C07D 239/54
[52] U.S. Cl. .................... 514/269; 544/309; 544/310; 544/311; 544/312
[58] Field of Search .................... 514/269, 274; 544/309, 310, 311, 312

[56] References Cited

U.S. PATENT DOCUMENTS

| | | | |
|---|---|---|---|
| 3,422,107 | 1/1969 | Mohler et al. | 544/271 |
| 3,734,911 | 5/1973 | Bestian | 544/271 |
| 3,737,433 | 6/1973 | Mohler et al. | 544/271 |
| 3,896,127 | 7/1975 | Takahashi et al. | 544/271 |
| 3,984,413 | 10/1976 | Metz et al. | 544/271 |
| 4,153,803 | 5/1979 | Thiele et al. | 544/271 |
| 4,275,064 | 6/1981 | Bodor et al. | 544/271 |
| 4,302,438 | 11/1981 | Zech | 544/271 |
| 4,460,772 | 7/1984 | Benovic et al. | 544/271 |
| 4,515,795 | 5/1985 | Hinze et al. | 544/267 |
| 4,576,947 | 3/1986 | Hinze et al. | 544/267 |
| 4,636,507 | 1/1987 | Kreutzer et al. | 544/263 |
| 4,737,502 | 4/1988 | Busacca | 514/265 |
| 4,833,146 | 5/1989 | Gebert et al. | 544/267 |
| 4,965,271 | 10/1990 | Mandell et al. | 514/263 |
| 5,039,666 | 8/1991 | Novick, Jr. | 514/37 |
| 5,096,906 | 3/1992 | Mandell et al. | 514/263 |
| 5,112,827 | 5/1992 | Saunders et al. | 514/263 |
| 5,118,500 | 6/1992 | Hänel et al. | 514/21 |
| 5,288,721 | 2/1994 | Klein et al. | 514/263 |
| 5,470,878 | 11/1995 | Michnick et al. | 514/558 |
| B1 3,737,433 | 6/1973 | Mohler et al. | 544/271 |

FOREIGN PATENT DOCUMENTS

| | | |
|---|---|---|
| 0 049-494 | 4/1982 | European Pat. Off. . |
| 0 157-284 | 10/1985 | European Pat. Off. . |
| 1011888 | 7/1957 | Germany . |
| 1118204 | 11/1961 | Germany . |
| 3167-186 | 7/1991 | Japan . |

OTHER PUBLICATIONS

Bianco et al., *Blood*, 76: Supplement 1 (522), p. 133a, "Pentoxifylline (PTX) and GM–CSF Decrease Tumor Necrosis Factor–ALPHA (TNF–α) Levels in Patients Undergoing Allogeneic Bone Marrow Transplantation (BMT)", 1990.

Bryce et al., *Arzneim.–Forsch./Drug Res.*, 39:4, pp. 512–517. "Metabolism and Pharmacokinetics of $^{14}$ C–Pentoxifylline in Healthy Volunteers", 1989.

Davis et al., *Applied Environment Microbiol.*, 48:2, pp. 327–331, "Microbial Models of Mammalian Metabolism: Microbil Reduction and Oxidation of Pentoxifylline", 1984.

Primary Examiner—Yogendra N. Gupta
Attorney, Agent, or Firm—McDermott, Will & Emery

[57] ABSTRACT

Therapeutic compounds with at least one carboxylic acid, ester or amide-substituted side chain have the formula:

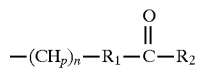

wherein j is an integer from one to three. The core moiety is non-cyclic or cyclic (carbocyclic or heterocyclic). R may be selected from among hydrogen, halogen, hydroxyl, amino, substituted or unsubstituted $C_{(1-10)}$ alkyl, $C_{(2-10)}$ alkenyl, carbocyclic or heterocyclic groups and at least one R has the formula I:

$$-(CH_p)_n-R_1-\overset{O}{\overset{\|}{C}}-R_2 \qquad I$$

wherein: one or two p are the integer one, otherwise p is two; and n is an integer from three to twenty; $R_1$ is selected from the group consisting of substituted and unsubstituted $CH_2$; $NR_3$, $R_3$ being hydrogen, substituted or unsubstituted $C_{(1-20)}$ alkyl, $C_{(1-20)}$ alkoxyl, $C_{(2-20)}$ alkenyl or $C_{(1-20)}$ hydroxyalkyl, or carbocyclic or heterocyclic group; O; —$CHR_4O$—, $R_4$ being substituted or unsubstituted $C_{(1-20)}$ alkyl, $C_{(1-20)}$ alkoxyl, $C_{(2-20)}$ alkenyl, $C_{(1-20)}$ hydroxyalkyl, or $R_2$ and $R_4$ join to form a substituted or unsubstituted heterocycle having four to seven ring atoms, the ether group —O— of —$CHR_4O$— being a member of the heterocycle. $R_2$ is selected from the group consisting of hydrogen; halogen; substituted or unsubstituted $C_{(1-10)}$ alkyl; $C_{(1-10)}$ alkoxyl; $C_{(2-10)}$ alkenyl; $C_{(1-10)}$ hydroxyalkyl; —$A(R_5)_m$, A being N or O, m being one or two and $R_5$ being hydrogen, a substituted or unsubstituted $C_{(1-10)}$ alkyl, $C_{(1-10)}$ alkoxyl, $C_{(2-10)}$ alkenyl or $C_{(1-10)}$ hydroxyalkyl), or carbocyclic or heterocyclic group. At least one of $R_1$ is $NR_3$, O or —$CHR_4O$—, or $R_2$ is —$A(R_5)_m$. The compounds and pharmaceutical compositions thereof are useful as therapies for diseases advanced via intracellular signaling through specific intracellular signaling pathways by mediating a signaling response to an external stimuli.

6 Claims, 5 Drawing Sheets

THERAPEUTIC COMPOUNDS CONTAINING PYRIMIDINYL MOIETIES

CROSS-REFERENCE TO RELATED APPLICATION

This is a Continuation-in-Part patent application of U.S. patent application Ser. No. 08/199,368, which was filed on Feb. 18, 1994 abandoned.

TECHNICAL FIELD OF THE INVENTION

The invention provides a group of compounds that are effective agents for inhibiting specific cellular signaling events often induced by inflammatory stimuli, or to be directly or indirectly antimicrobial to yeast or fungal infections. More specifically, the inventive compounds have at least one carboxylic acid, ester or amide-substituted chain bonded to a core moiety. The inventive compounds are, among other things, useful antagonists to control intracellular levels of specific sn-2 unsaturated phosphatidic acids and corresponding phosphatidic acid-derived diacylglycerols, intracellular cell signaling messengers which occur in response to pro-inflammatory proliferative stimuli.

BACKGROUND OF THE INVENTION

Pentoxifylline (1-(5-oxohexyl)-3,7-dimethylxanthine), abbreviated PTX, is a xanthine derivative which has seen widespread medical use for the increase of blood flow. PTX is disclosed in U.S. Pat. Nos. 3,422,107 and 3,737,433, both to Mohler et al. Metabolites of PTX were summarized in Davis et al., *Applied Environment Microbiol.* 48:327, 1984. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947 to Hinze et al. Other metabolites, 1-(5-pentyl)-3,7-dimethylxanthine carboxylic acid, designated M5, and 1-(4-butyl)-3,7-dimethylxanthine carboxylic acid, designated M5, were disclosed by Bryce et al., *Arzneim.-Forsch./Drug Res.* 39(4):512–517, 1989. In addition, U.S. Pat. Nos. 4,833,146 and 5,039,666 to Gebert et al. and Novick, Jr., respectively, disclose use of tertiary alcohol analogs of xanthine for enhancing cerebral blood flow.

PTX and its known metabolites thereof have been shown to have in vivo activity in specific biologic systems. U.S. Pat. No. 4,636,507 to Kreutzer et al. describes an ability of PTX and M1, to further promote chemotaxis in polymorphonuclear leukocytes responding to a chemotaxis stimulator. In addition, PTX and related tertiary alcohol substituted xanthines inhibit activity of certain cytokines to affect chemotaxis (U.S. Pat. Nos. 4,965,271 and 5,096,906 to Mandell et al.). By administrating PTX and GM-CSF, patients undergoing allogeneic bone marrow transplant exhibited decreased levels of tumor necrosis factor, TNF, (Bianco et al., *Blood* 76: Supplement 1 (522A), 1990). Reduction in assayable levels of TNF was accompanied by a reduction in bone marrow transplant-related complications. However, in normal volunteers, TNF levels were higher among PTX recipients. Therefore, elevated levels of TNF are not the primary cause of such complications.

Further research with PTX, its metabolites and their activity relating to various biologic systems spurred investigations with potential therapeutic agents heretofore unknown. These agents were identified as potential therapies for treating or preventing disease by inhibiting secondary cellular response to an external or in situ primary stimuli. These investigations sought to identify efficacious therapeutic compounds which were safe and effective for human or animal administration and maintain cellular homeostasis in the face of a variety of inflammatory stimuli.

In undertaking these investigations, previously unknown therapeutic compounds were discovered. These novel compounds are discussed herein. These compounds exhibit remarkable characteristics in predictive in vitro disease assays, which known compounds do not possess, indicating efficacious therapies for treating or preventing disease using the inventive compounds.

SUMMARY OF THE INVENTION

The invention provides carboxylic acid, ester and amide-substituted therapeutic compounds and pharmaceutical compositions and uses thereof. The inventive carboxylic acid, ester or amide-substituted compounds are useful in a large variety of therapeutic indications for treating or preventing disease. In particular, the inventive compounds and pharmaceutical compositions thereof provide therapy for diseases caused or advanced by intracellular signaling through specific intracellular signaling pathways, specifically the pathways discussed herein, by mediating a signaling response to an external stimuli. Abnormally-induced intracellular signaling is characteristic of diseases treatable using the inventive compounds or pharmaceutical compositions thereof.

The inventive compounds have at least one carboxylic acid, ester or amide-containing side chain and are preferably carbocyclic or heterocyclic compounds. The inventive compounds and pharmaceutical compositions thereof have the formula:

CORE MOIETY—(R)$_j$ including resolved enantiomers and/or diastereomers, hydrates, salts, solvates and mixtures thereof, wherein j is an integer from one to three, the core moiety is non-cyclic or cyclic (carbocyclic or heterocyclic) and R may be selected from among: hydrogen, halogen (preferably bromine, chlorine, fluorine and iodine), hydroxyl, amino, substituted or unsubstituted $C_{(1-10)}$ alkyl, $C_{(2-10)}$ alkenyl, carbocyclic or heterocyclic groups and formula I. The inventive compounds have at least one R of the following formula I:

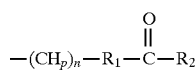

wherein:
one or two p are the integer one, otherwise p is two;
n is an integer from three to twenty, preferably seven to sixteen, most preferably five to sixteen.
$R_1$ can be selected from the group consisting of substituted and unsubstituted $CH_2$; $NR_3$, $R_3$ being hydrogen, substituted or unsubstituted $C_{(1-20)}$ alkyl, $C_{(1-20)}$ alkoxyl, $C_{(2-20)}$ alkenyl or $C_{(1-20)}$ hydroxyalkyl, or carbocyclic or heterocyclic group; O; —$CHR_4O$—, or —$C(R_4)_rO$—, r being one or two, $R_4$ being =O, hydrogen, substituted or unsubstituted $C_{(1-20)}$ alkyl, $C_{(1-20)}$ alkoxyl, $C_{(2-20)}$ alkenyl, $C_{(1-20)}$ hydroxyalkyl, $C_{(1-20)}$ aminoalkyl, —$(CH_2)_qA(R_5)_m$, q being an integer from one to four, A being N or O, m being one or two and $R_5$ being hydrogen, a substituted or unsubstituted $C_{(1-10)}$ alkyl, $C_{(1-10)}$ alkoxyl, $C_{(2-10)}$ alkenyl or $C_{(1-10)}$ hydroxyalkyl, $C_{(1-10)}$ aminoalkyl, carbocyclic or heterocyclic group, or $R_2$ and $R_4$ join to form a substituted or unsubstituted heterocycle having four to seven ring atoms, the —O— of —CHR$_4$O— being a member of the heterocycle.

R$_2$ can be selected from the group consisting of hydrogen; halogen; substituted or unsubstituted C$_{(1-10)}$ alkyl; C$_{(1-10)}$ alkoxyl; C$_{(2-10)}$ alkenyl; C$_{(1-10)}$ hydroxyalkyl, C$_{(1-20)}$ aminoalkyl; —A(R$_5$)$_m$; —CHR$_6$A(R$_5$)$_m$; A, R$_5$ and m being defined above, R$_6$ being a substituted or unsubstituted C$_{(1-20)}$ alkyl, C$_{(1-20)}$ alkoxyl, C$_{(2-20)}$ alkenyl, C$_{(1-20)}$ hydroxyalkyl, C$_{(1-20)}$ aminoalkyl, carbocyclic or heterocyclic groups, or A is N, m is two and the two R$_5$ join to form a substituted or unsubstituted heterocycle having from four to seven ring atoms, A comprising a hetero atom of the heterocycle.

In the inventive compounds, at least one of R$_1$ is NR$_3$, O or —CHR$_4$O—, or R$_2$ is —A(R$_5$)$_m$. Optionally, (CH$_2$)$_n$ may 1) be substituted by a halogen, hydroxide, substituted or unsubstituted C$_{(1-10)}$ alkyl, C$_{(2-10)}$ alkenyl, C$_{(1-10)}$ alkoxyl, C$_{(1-10)}$ acyloxy, C$_{(1-10)}$ oxyalkyl, carbocyclic or heterocyclic group; 2) have one or two unsaturated bonds (preferably in a cis configuration); or 3) be interrupted by at least one oxygen atom.

A non-cyclic core moiety may include, but is not limited to, for example, acetamide, amide, amine, amino acid (one or two), carboxide, ester, terminal halogen or hydrogen atom, hydroxide, glutaric acid, glycine derivative, ketone, phosphate, phosphonate, sulfate, sulfonate, sulfone, sulfoxide, simple ionic functional group, thiol, thiolester or the like. Exemplary core moiety amino acids may include, but are not limited to, one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be an amide, carboxyl ester, carboxide, hydrogen, hydroxide or a dipeptide comprising two amino acids selected from the foregoing exemplary list. A non-cyclic, halogen-core moiety may be, for example, bromine, chlorine, fluorine or iodine.

A cyclic core may be at least one five- to seven-member, non-heterocyclic ring (i.e., carbocycle) or a heterocycle. The at least one five- to seven-membered cyclic core may preferably have from one to three, five- to six-membered ring structures in a predominantly planar configuration. An exemplary, non-heterocyclic ring core moiety may be selected from the group consisting of substituted or unsubstituted benzene; biphenyl; cyclohexane; cyclohexanedione; cyclopentanedione; napthlalene; phenol; quinone; salicylic acid; stilbene and tricyclododecane.

Although other heterocyclic cores are within the scope of the invention, the following representatives are preferred: substituted or unsubstituted barbituric acid; benzamide; lactam; glutarimide; homophthalimide; hydrophthalimide; imidazole; imidazole amide; indomethacin; isocarbostyril; lumazine; N-alkylheterocyclic; N-heterocyclic; pteridine; pthalimide; piperidine; pyridine; pyrimidine; pyrrole amide; quaternized N-heterocyclic; quinolizinedione; quinazolinone; quinoline; recorsinol; succinimide; theobromine; thymine; triazine; uric acid; uracil; vitamins A, E or K; or xanthine.

Preferably, R is bonded to a nitrogen of the core moiety, if present, most preferably to the nitrogen of a glutarimide, methylthymine, thymine, uracil or xanthine core. In representative, preferred compounds, R having formula I may be bonded to an N$_1$ nitrogen of xanthine (and N$_3$ and N$_7$ xanthine nitrogens may be independently substituted by a member selected from the group consisting of hydrogen, C$_{(1-6)}$ alkyl, fluoro, chloro and amino); or N$_1$ nitrogen of uracil. Alternatively, R having formula I may be bonded to N$_1$ and N$_3$ xanthine nitrogens and the N$_7$ xanthine nitrogen is substituted by a member selected from the group consisting of hydrogen, methyl, fluoro, chloro and amino. Representative, preferred inventive compounds are compounds of formulas II, III and IV:

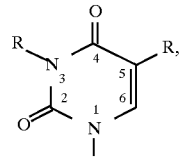

II

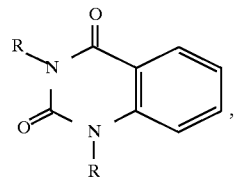

III

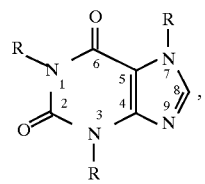

IV wherein R is as defined above.

The invention also provides a pharmaceutical composition. Pharmaceutical compositions of the inventive compounds comprise a pharmaceutical carrier or diluent and some amount of an inventive compound. The nature of the composition and the pharmaceutical carrier or diluent will, of course, depend upon the intended route of administration, for example, parenterally, topically, orally or by inhalation for treatment of a patient with disease symptoms.

The invention also provides a method for treating an individual having a variety of diseases. The disease is characterized by or can be treated by inhibiting an immune response or a cellular response to external or in situ primary stimuli. Treatment of the disease states involves mediating the cellular response through a specific phospholipid-based second messenger acting adjacent to a cell membrane inner leaflet. The second messenger pathway is activated in response to various noxious or proliferative stimuli, characteristic of disease states treatable using the inventive compounds or pharmaceutical compositions thereof. Biochemistry of this second messenger pathway is described herein. More specifically, the invention includes methods for treating or preventing clinical symptoms of various disease states or reducing toxicity of other treatments by inhibiting cellular signaling through a second messenger pathway involving signaling through phosphatidic acid and through glycan phosphatidylinositol (Gly PI).

Gly PI consists of a phosphatidylinositol-1-phosphate (PIP) bound through the carbon 6-hydroxyl to a glucosamine residue, which in turn is bound, usually to 2–5 other glycan residues (1→4 type, linear bonds) containing an additional one to three phosphoethanolamine moieties, the last of which may be bound to an external protein such as Thy-1. Evidence suggests a broad variety of structural variation in the sn-1 and sn-2 positions of the glycerollipid moiety of the phosphatidylinositol, as well as fatty acyl addition to the 2—OH group of the inositol. Several functional parameters of structure have been observed, the most remarkable of which point to a minimum presence of at least one myristoyl sidechain in Gly-PI molecules, the presence of both alkyl (ether) and snacyl chains in the sn-1 position, and the presence of palminate (C16:0) in the 2—OH position of the inositol in protein-binding Gly-PI. Thomas et al., *Biochemistry* 29: 5413–5422 (1991).

Recent research has demonstrated that 2—OH-acylation of the inositol moiety conveys resistance to hydrolysis with Gly PI-directed phospholipase C ($P_tG$-PLC, a phosphodiesterase which hydrolyzes Gly PI to glycan inositol phosphate and diacylglycerol) but not to Gly PI-directed phospholipase D ($P_tG$-PLD, a phosphodiesterase which hydrolyzes Gly PI to glycan inositol+phosphatidic acid).

Research has identified two functions of Gly-PI: 1) external protein binding, the purpose of which may be simple binding to the cell membrane or placement of conformational constraints on the structure of externally bound membrane proteins (e.g., so that a particular portion of the molecule faces an extracellular environment); and 2) signal transduction, including part of the intracellular signal sent by insulin and a detectable portion of the signal transduced by Interleukin-2 (IL-2). We have found that signal transducing Gly-PI in B lymphocytes is hydrolyzed following anti-mu crosslinking, and then resynthesized rapidly. In these systems, two Gly-PI species are synthesized: a) $GlyPI_1$, containing 1-myristoyl 2-palmitoyl, 1-o-tetradecanyl (myristyl) 2-palmitoyl and 1-myristyl 2-myristyl phosphatidylinositol; and b) Gly $PI_2$, containing 1-myristoyl 2-oleoyl and 1-o-myristyl 2-linoleoyl phosphatidylinositol. Fraction (a) above contains a 1:1 mole content of C22 or C20 acyl groups attached to the inositol phosphate. The Gly-$PI_1$ fraction, identified by glucosamine labeling followed by mass spectrometry, exhibits a characteristic tripartite peak (glycan-inositol: 2-OH-acyl: phosphatidic acid moieties) and is uniformly inositol 2-OH acylated. Therefore, fraction (a) conveys resistance to $P_tG$-PLC but not to $P_tG$-PLD, suggesting that the observed fraction, when hydrolyzed, will generate 1-myristyl and 1-o-myristyl phosphatidic acid species, subsequently observed.

Thus, inventive compounds, useful in treating diseases and reducing toxicity of other disease treatments, would affect cellular signaling through a second messenger pathway by interacting with binding and/or signaling functions of Gly PI.

A disease state or treatment-induced toxicity are selected from the group consisting of: tumor progression involving tumor stimulation of blood supply (angiogenesis) by production of fibroblast growth factor (FGF), vascular endothelial growth factor (VEGF) or platelet-derived growth factor (PDGF); tumor invasion and formation of metastases through adhesion molecule binding, expressed by vascular endothelial cells (VCAM and ICAM); tissue invasion through tumor metalloprotease production such as MMP-9; autoimmune diseases caused by dysregulation of the T cell or B cell immune systems, treatable by suppression of the T cell or B cell responses; acute allergic reactions including, but not limited to, asthma and chronic inflammatory diseases, mediated by pro-inflammatory cytokines including tumor necrosis factor (TNF) and IL-1, and rheumatoid arthritis, osteoarthritis, multiple sclerosis or insulin dependent diabetes mellitus (IDDM), associated with enhanced localization of inflammatory cells and release of inflammatory cytokines and metalloproteases; smooth muscle cell, endothelial cell, fibroblast and other cell type proliferation in response to growth factors, such as PDGF-AA, BB, FGF, EGF, etc. (ie., atherosclerosis, restenosis, stroke, and coronary artery disease); activation of human immunodeficiency virus infection (AIDS and AIDS related complex); HIV-associated dementia; kidney mesangial cell proliferation in response to IL-1, MIP-1α, PDGF or FGF; inflammation; kidney glomerular or tubular toxicity in response to cyclosporin A or amphotericin B treatment; organ toxicity (e.g., gastrointestinal or pulmonary epithelial) in response to a cytotoxic therapy (e.g., cytotoxic drug or radiation); effects of non-alkylating anti-tumor agents; inflammation in response to inflammatory stimuli (e.g., TNF, IL-1 and the like) characterized by production of metalloproteases or allergies due to degranulation of mast cells and basophils in response to IgE or RANTES; bone diseases caused by overproduction of osteoclast-activating factor (OAF) by osteoclasts; CNS diseases resulting from over-stimulation by pro-inflammatory neurotransmitters such as, acetylcholine, serotonin, leuenkephalin or glutamate; acute inflammatory diseases such as septic shock, adult respiratory distress syndrome; multi-organ dysfunction associated with inflammatory cytokine cascade; and combinations thereof.

In a large number of cells, signaling is dependent upon generation of a broad variety of PA species, some of which are generated from lyso-PA by the enzyme lyso-PA acyl transferase and some of which are generated from 2-O—acyl glycan-PI by $P_tG$-PLD. Generation of each of these PA species (the predominant forms being: 1-acyl and 1-alkyl 2-linoleoyl PA compounds, generated by LPAAT; and 1-myristyl 2-palmitoyl and 1-o-myristyl 2-palmitoyl, generated by $P_tG$-PLD) serves to effect both proliferative and/or inflammatory signaling in the diseases discussed and cell systems described above.

The inventive compounds are of particular significance for inhibiting IL-2-induced proliferative response. IL-2 signaling inhibition is potentially useful in the treatment of numerous disease states involving T-cell activation and hyperproliferation. Exemplary autoimmune diseases treated by inhibiting IL-2 signaling are lupus, scleroderma, rheumatoid arthritis, multiple sclerosis, glomerula nephritis as well as potential malignancies, including but not limited to, chronic myelogenous leukemia as well as others.

DETAILED DESCRIPTION OF PREFERRED EMBODIMENTS

Figure 1:
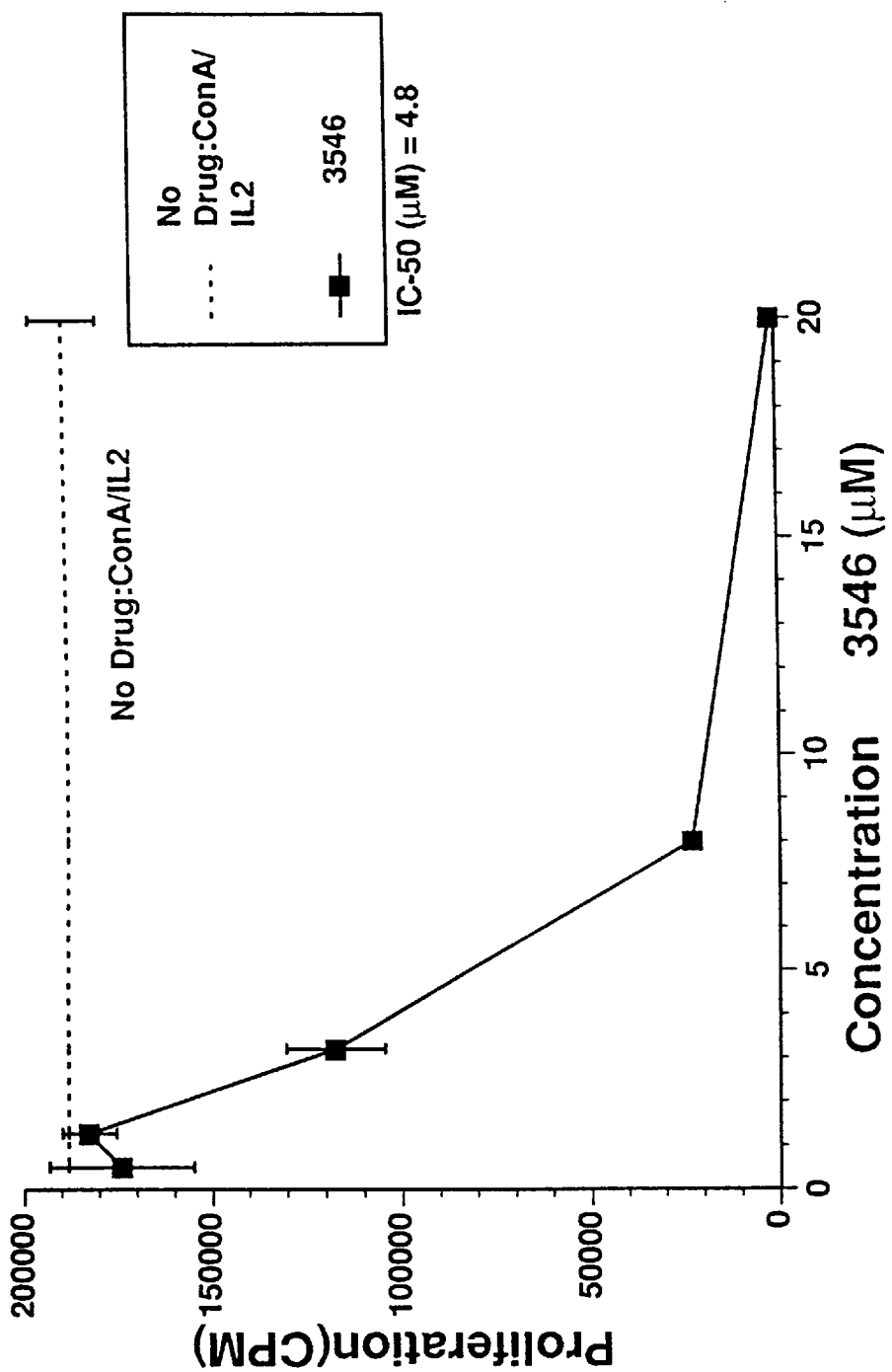
FIGS. 1 and 2 are dose response curves prepared from results in a murine thymocyte assay, determining inhibitive effects of inventive compounds nos. 3546 and 3549, (see below for chemical name and structure) respectively, on proliferation of thymocytes co-stimulated by ConA and IL-2.

The invention provides a genus of compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A2.
PLD=phospholipase D
PAA=phosphoarachidonic acid
PC=phosphatidyl choline "remodeled" PA, cyclic pathway=PAA, LPA, PA and DAG intermediates substituted with 1-saturated, 2-linoleoyl or 1,2-dioleoyl, dioleoyl/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaenoyl- side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. Administration of the compounds of the invention reverse this elevation.

The compounds and pharmaceutical compositions of the invention include, but are not limited to, inhibitors of subspecies of LPAAT and PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2- diunsaturated and 1-alkyl, 2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

Each membrane phospholipid subclass (e.g., PA, PI, PE, PC and PS) reaches a stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmitate. In resting cells, PC's acyl side chains consist mostly of acyl palmitate in the sn-1 position and oleate in the sn-2 position. PE and PI are predominantly composed of sn-1 stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. It is important to know whether or not each phospholipid species passes through a PA form prior to hydrolysis to DAG. The lyso-PA that is converted to PA and then to DAG may be shown. The complexities of this second messenger pathway can be sorted by suitable analyses using fatty acyl side chain chemistry (e.g., by thin layer chromatography, gas-liquid chromatography, or high pressure liquid chromatography) of intermediates in cells at various time points after stimulation of the second messenger pathway.

In certain mesenchymal cells, such as neutrophils and rat or human mesangial cells, several signaling pathways may be activated in tandem, simultaneously or both. For example, in neutrophils, F-Met-Leu-Phe stimulates formation of PA through the action of PLD, followed in time by formation of DAG through PAPH action. Several minutes later, DAG is generated from PI through the classical phosphoinositide pathway. In many cells, DAG is derived from both PA that is remodeled through a cycle whereby PA is sn-2 hydrolyzed by PLA2, followed by sn-2 transacylation by LPAAT and PA that is generated in a PLD-pathway from either PE or PC or both substrates by PLD.

The present second messenger pathway involves substrates with unsaturated fatty acids in the sn-2 position other than arachidonate and those sub-species of PAPH and LPAAT that are not involved in normal cellular housekeeping functions that are part of the classical PI pathway. The PAPH and LPAAT enzymes involved in this specific second messenger pathway are exquisitely stereo-specific for different acyl side chains and isomeric forms of substrates. Therefore, the inventive compounds may preferably be substantially enantiomerically pure.

PTX (in vitro) blocks formation of remodeled PA through the PA/DAG pathway at high PTX concentrations (greater than those that could be achieved in patients without dose-limiting side effects) by blocking formation of PA subspecies at LPAAT. Even in the presence of PTX, cells continue to form PA through the action of PLD, and DAG is also formed through the action of phospholipase C on PC and PI. The latter pathway are not inhibited by the inventive compounds or PTX. In PTX-treated cells, DAG derived from remodeled and PLA-generated PA is diminished (e.g., 1,2-sn-dioleoyl DAG, 1-alkyl, 2-linoleoyl DAG and 1-alkyl, 2-docosahexaneolyl DAG). Therefore, the inventive compounds and PTX inhibit the formation of only a certain species of PA and DAG by selectively inhibiting a specific second messenger pathway that is only activated in cells by noxious stimuli, but is not used to signal normal cellular housekeeping functions.

Therapeutic Uses of the Inventive Compounds

The specific activation inhibition of the second messenger pathway, as described above and activated primarily by various noxious stimuli, suggests that the inventive compounds are useful in treating a wide variety of clinical indications, mediated at the cellular level by a common mechanism of action. Moreover, in vitro and in vivo data presented herein provides predictive data that a wide variety of clinical indications, having similar effects on the specific second messenger pathway (activated by noxious stimuli and mediated through, for example, inflammatory cytokines), may be treated by the inventive compounds, which specifically inhibit the pathway. In fact, the mechanism of action for the inventive compounds explains why these compounds have multifarious clinical indications.

Activation of the second messenger pathway is a major mediator of response to noxious stimuli and results in cellular signals that lead to, for example, acute and chronic inflammation, immune response and cancer cell growth. Although the inventive compounds may desirably inhibit other noxious stimuli not discussed, they most effectively mediate the above conditions. Signals mediated by the present second messenger pathway include, for example, those cellular responses of LPS directly; T cell activation by antigen; B cell activation by antigen, cellular responses to IL-1, mediated through the IL-1 Type I receptor (but not the IL-1 Type II receptor), and TNF (Type I receptor), growth stimulated by transformations including, but not limited to, activated oncogenes (e.g., ras, abl, her 2-neu and the like), smooth muscle cell proliferation stimulated by PDGF, b-FGF and IL-1; T cell and B cell growth stimulation by IL-2, IL-4 or IL-7 and IL-4 or IL-6, respectively; and more generally, T cell receptor signaling.

In vitro, the inventive compounds: (1) block IL-1 signal transduction through the Type 1 receptor as shown, for example, by preventing IL-1 and IL-1 plus PDGF (platelet derived growth factor) induction of proliferation of smooth muscle, endothelial and kidney mesengial cells; (2) suppress up-regulation of adhesion molecules as shown, for example, by blocking VCAM in endothelial cells; (3) inhibit TNF, LPS and IL-1 induced metalloproteases (an inflammation model); (4) block LPS, TNF or IL-1 induced metalloprotease and secondary cytokine production (for prevention and treatment of septic shock); (5) suppress T cell and B cell activation by antigen, for example, IL-2 and IL-4; (6) inhibit mast cell activation by IgE; (7) are cytotoxic for transformed cells and tumor cell lines, yet not for normal cells; and (8) block signaling by IL-2, IL-4, IL-6 and IL-7 on T and B cells.

The foregoing in vitro effects give rise to the following in vivo biological effects, including, but not limited to: protection and treatment of endotoxic shock and sepsis induced by gram positive or gram negative bacteria; inhibition of tumor cell growth; synergistic immunosuppression, active in autoimmune diseases and in suppressing allograft reactions; and stimulation of hair grow through reversal of an apoptotic process. The inventive compounds are most potent when used to prevent and treat septic shock, treat acute and chronic inflammatory disease, treat or prevent an autoimmune disease and stimulate hair growth (when applied topically).

The inventive compounds also are useful as an adjuvant to inhibit toxic side effects of drugs whose side effects are mediated through the present second messenger pathway.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus bFGF, a 72 Kd type IV collagenase that is usually constitutive and induced by TNF or IL-1, and a stromelysinPUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. Accordingly, the inventive compounds prevent induction of certain metalloproteases induced by IL-1 or TNF and are not involved with constitutively produced proteases (e.g., 72 kD type IV collagenase) involved in normal tissue remodeling.

The inventive compounds inhibit signal transduction mediated through the Type I IL-1 receptor, and are therefore considered as IL-1 antagonists. A recent review article entitled "The Role of Interleukin-1 in Disease" (Dinarello et al., $N.$ $Engl.$ $J.$ $Med.$ 328, 106, Jan. 14, 1993) described the role of IL-1 as "an important rapid and direct determinant of disease . . . In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." The article describes a group of diseases that are mediated by IL-1, including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above-mentioned diseases.

For example, for sepsis syndrome, the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure and doses of 300 ng or more per kilogram of body weight may cause severe hypotension. The therapeutic advantage of blocking the action of IL-1 resides in preventing its deleterious biological effects without interfering with the production of molecules that have a role in homeostasis. The present inventive compounds address this need, identified by Dinarello et al., by inhibiting cellular signaling only through the IL-1 Type I receptor and not through the IL-1 Type II receptor.

With regard to rheumatoid arthritis, Dinarello and Wolff state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ ($PGE_2$), leukotriene $B_4$ ($LTB_4$) and IL-8, an inflammatory cytokine with neutrophil-chemoattractant and neutrophil-stimulating properties. Tissue concentrations of PGE2 and LTB4 correlate to severity of disease in patients with ulcerative colitis, patients with inflammatory bowel disease having high tissue concentrations of IL-1 and IL-8. Therefore, an IL-1 antagonist, such as the inventive compounds, would be effective to treat inflammatory bowel disease.

With regard to acute and chronic myelogenous leukemia, there is increasing evidence that IL-1 acts as a growth factor for such tumor cells. Therefore, the inventive compounds should be effective to prevent the growth of worsening of disease for acute and chronic myelogenous leukemias.

Insulin-dependent diabetes mellitus (IDDM) is considered to be an autoimmune disease with destruction of beta cells in the islets of Langerhans, mediated by immunocompetent cells. Islets of animals with spontaneously occurring IDDM (e.g., BB rats or NOD mice) have inflammatory cells that contain IL-1. Therefore, the inventive compounds should be useful for the preventing and treating IDDM.

IL-1 also plays a role in atherosclerosis development. Endothelial cells are a target of IL-1. IL-1 stimulates proliferation of vascular smooth muscle cells. Foam cells, isolated from fatty arterial plaques from hypercholesterolemic rabbits, contain IL-1β and IL-1β messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds should be useful in preventing and treating atherosclerosis.

IL-1 activates (through the Type I IL-1 receptor) a lyso-PA acyltransferase (LPAAT) and phosphatidate phosphohydrolase within 5 seconds of cell (for example, human mesangial cells, HMC) exposure to this cytokine. As discussed in detail above, activation of both enzymes results in production of PA species with sn-1 and sn-2 unsaturated acyl groups, with the majority of sn-2 acyl chains being polyunsaturated. Both IL-1 and a product of LPAAT, 1,2-sn-dilinoleoyl PA, activate a signaling pathway involving hydrolysis of PE to PA. This reaction is followed by dephosphorylation of PA to produce both 1,2-sn-diacylglycerol, and 1-o-alkyl, or 1-o-alkenyl,acylglycerol (AAG) species. The inventive compounds exert their activity by inhibiting one or both enzymes at an inner leaflet of the plasma membrane. Therefore, appropriate in vitro models for drug activity may measure inhibition of stimulation caused by a proinflainmatory cytokine or other inflammatory cellular signal.

The generation of the sn-2 unsaturated PA fraction by LPAAT serves to activate either G-proteins, or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of di-unsaturated PA, which is less than about 0.1% of total membrane lipid mass, is sufficient to activate PLD activity. This quantity of PA is similar to that endogenously synthesized by LPAAT. The PA-stimulated PLD acts upon PE, which should be localized to the inner leaflet of the cell membrane, enriched in PE relative to the outer leaflet. Therefore, the cellular inflammatory response to IL-1 is mediated by the pathway: IL-1R→PA→(PLD)→PE. Whereas a localized tissue response is: lysoPA→PI→PKC→(PLD)→PC. The PLD species are likely to be different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e., >30 minutes) is maintained by PC-derived PA generated by PC-directed PLD. Therefore, the pathway inhibited by the inventive compounds is PE-directed and not PC-directed. Moreover, the PE-directed PLD favors substrates with sn-2 long-chain unsaturation.

DAG and PA are upregulated in oncogenically transformed cells. For example, activating ras mutations result in increased generation of DAG upon stimulation with mitogens, although the sources of DAG differ between experimental systems. In nontransformed renal mesangial cells, IL-1β stimulation increased PLA2 and LPAAT activation, resulting in generation of sn-2 unsaturated PA and subsequent hydrolysis to DAG by phosphatidate phosphohydrolase. The ras transformation in NIH/3T3 cells upregulates serum-stimulated generation of DAG and PA. Particular species of DAG that is stimulated by serum is dioleoyl and of PA are dilinoleoyl and dioleoyl. This upregulation occurs over 4–12 hours and pretreatment of cells with an inventive compound, or PTX, blocks generation of these phospholipid second messengers. The inhibition occurs either through suppressing the generation of PA de novo from lysoPA, or through inhibition of one or both arms of the Lands cycle. The coordinate increase of lysoPA in the setting of diminished PA/DAG production suggests inhibition of transacylation of a precursor lipid. Therefore, the ras transformation mediates an upregulation of PA through indirect stimulation of PLA2 and/or LPAAT activity. The inventive compounds inhibit the conversion of the upregulated lysoPA to PA and subsequently block the phenotypic changes induced by PA/DAG in the membrane.

The ability of the inventive compounds to inhibit generation of unsaturated phospholipids is mirrored by the ability of inventive compounds to inhibit proliferation and tumorigenicity of ras-transformed cells in vitro and in vivo. PTX inhibits ras-transformed NIH/3T3 cells more than parental cells. This inhibition is reversible and is not associated with significant cytotoxicity.

Excessive or unregulated TNF (tumor necrosis factor) production is implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, AIDS, other viral infections (e.g., CMV, influenza, adenovirus, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled through the present second messenger cellular phospholipid-based signaling pathway and by excessive or unregulated production of "first messenger" inflammatory cytokines such as TNF or IL-1. With regard to TNF first messenger signaling, there are several disease states in which excessive or unregulated TNF production by monocytesmacrophages is implicated in exacerbating or causing the disease. These include, but are not limited to, for example, neurodegenerative diseases such as Alzheimers disease, endotoxemia or toxic shock syndrome (Tracey et al., Nature 330:662, 1987 and Hinshaw et al., Circ. Shock 30:279, 1990); cachexia (Dezube et al., Lancet 355:662, 1990), and adult respiratory distress syndrome (Miller et al., Lancet 2(8665):712, 1989). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., N. Engl. J. Med. 320:1585, 1989), chronic pulmonary inflammatory diseases such as silicosis and asbestosis (Piguet et al., Nature 344:245, 1990, and Bissonnette et al., Inflammation 13:329, 1989), and reperfusion injury (Vedder et al., Proc. Natl. Acad. Sci. USA 87:2643, 1990).

The compounds of the invention can inhibit certain VEGF (vascular endothelial growth factor), FGF (fibroblast growth factor) and PDGF (platelet derived growth factor) effects in vivo, such as inhibition of angiogenesis or restenosis. For example, Ferns et al., Science 253:1129, 1991, have shown that neointimal smooth muscle chemotaxis and angioplasty are inhibited in rats using a neutralizing antibody to PDGF. Also, Jawien et al., J. Clin Invest. 89:507, 1992, have shown that PDGF promotes smooth muscle migration and intimal thickening in a rat model of balloon angioplasty. Inhibition of the PDGF-mediated effects following balloon angioplasty by the inventive compounds is the pharmacological rationale for using the inventive compounds as therapeutic agents to prevent restenosis. The inventive compounds also inhibit atherogenesis because increased levels of PDGF expressed by macrophages are associated with all phases of atherogenesis (Ross et al., Science 248:1009, 1990). Further, many human tumors express elevated levels of either PDGF, FGF, receptors for FGF or PDGF, or mutated cellular oncogenes highly homologous to these growth factors or their receptors. For example, such tumor cell lines include sarcoma cell lines (Leveen et al., Int. J. Cancer 46:1066, 1990), metastatic melanoma cells (Yamanishi et al., Cancer Res. 52:5024, 1992), and glial tumors (Fleming et al., Cancer Res. 52:4550, 1992).

The inventive compounds are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

Compounds of the Invention

The invention provides compounds that are useful therapeutic agents, inhibiting proinflammatory and neoplastic cellular signalling mechanisms. The inventive compounds and inventive pharmaceutical compositions thereof have the formula:

CORE MOIETY—(R)$_j$ including resolved enantiomers and/or diastereomers, hydrates, salts, solvates and mixtures thereof, wherein j is an integer from one to three, the core moiety is non-cyclic or cyclic (e.g. carbocyclic or heterocyclic) and R may be selected from among: hydrogen, halogen (preferably bromine, chlorine, fluorine and iodine), hydroxyl, amino, substituted or unsubstituted $C_{(1-10)}$ alkyl, $C_{(2-10)}$ alkenyl, carbocyclic or heterocyclic groups and formula I.

Preferred R substituents having a structure other than formula I include, but are not limited to, 2-bromopropyl, 4-chloropentyl, cyclohexyl, cyclopentyl, 3-dimethylaminobutyl, ethyl, hexyl, 2-hydroxyethyl, 5-hydroxyhexyl, 3-hydroxy-n-butyl, 3-hydroxypropyl, isobutyl, isopropyl, 2-methoxyethyl, 4-methoxy-n-butyl, methyl, n-butyl, n-propyl, phenyl, t-butyl and the like. Particularly preferred R having a structure other than formula I are ethyl, methyl, or hydrogen.

The inventive compounds have at least one R of the following formula I:

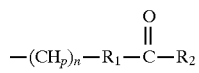

wherein:

one or two p are the integer one, otherwise p is two;

n is an integer from three to twenty.

$R_1$ is selected from among substituted and unsubstituted $CH_2$; $NR_3$ ($R_3$ being hydrogen, substituted or unsubstituted $C_{(1-20)}$ alkyl, $C_{(1-20)}$ alkoxyl, $C_{(2-20)}$ alkenyl or $C_{(1-20)}$ hydroxyalkyl, or carbocyclic or heterocyclic group); O; —CHR$_4$O—(R$_4$ being substituted or unsubstituted $C_{(1-20)}$ alkyl, $C_{(1-20)}$ alkoxyl, $C_{(2-20)}$ alkenyl, $C_{(1-20)}$ hydroxyalkyl or $R_2$ and $R_4$ join to form a substituted or unsubstituted heterocycle having four to seven ring atoms, the ether group —O— of —CHR$_4$O— being a member of the heterocycle); $R_2$ is hydrogen, halogen, substituted or unsubstituted $C_{(1-10)}$ alkyl, $C_{(1-10)}$ alkoxyl, $C_{(2-10)}$ alkenyl, $C_{(1-10)}$ hydroxyalkyl, —A(R$_5$)$_m$ (A being N or O, m being one or two and R$_5$ being hydrogen, a substituted or unsubstituted carbocyclic or heterocyclic group having at least one four- to seven-membered ring; substituted or unsubstituted $C_{(1-10)}$ alkyl, $C_{(1-10)}$ alkoxyl, $C_{(2-10)}$ alkenyl or $C_{(1-10)}$ hydroxyalkyl).

In the inventive compounds, at least one of $R_1$ is $NR_3$, O or —CHR$_4$O—, or $R_2$ is —A(R$_5$)$_m$. In addition when the core moiety is xanthine, $R_2$ is —A(R$_5$)$_m$, A is —O— and $R_5$ is hydrogen or $C_{(1-10)}$ alkyl, n is not less than four. Optionally, (CH$_2$)$_n$ may 1) be substituted by a halogen, hydroxide, substituted or unsubstituted $C_{(1-10)}$ alkyl, $C_{(2-10)}$ alkenyl, $C_{(1-10)}$ alkoxyl, $C_{(1-10)}$ acyloxy, $C_{(1-10)}$ oxyalkyl, carbocyclic or heterocyclic group; 2) have one or two unsaturated bonds (preferably in a cis configuration); or 3) be interrupted by at least one oxygen atom.

Preferably, n is an integer from about three to about eighteen, more preferably, an integer from about four to about ten. In especially preferred compounds, $R_1$ is $NR_3$, $R_3$ is $C_{(1-20)}$ alkyl, and $R_2$ is $C_{(1-10)}$ alkyl or hydroxyalkyl. Even more preferably, (CH$_2$)$_n$ is substituted by an hydroxide, a $C_{(1-10)}$ alkyl or $C_{(1-10)}$ acyloxy. Other preferred embodiments may include, but are not limited to, compounds in which $R_1$ is O, $R_2$ is $C_{(1-10)}$ alkyl, $C_{(2-10)}$ alkenyl or $C_{(1-10)}$ alkoxyl and (CH$_2$)$_n$ is substituted by a halo-substituted $C_{(1-10)}$ alkyl, or unsubstituted $C_{(2-10)}$ alkenyl or $C_{(1-10)}$ alkoxyl.

Although other possible substituents are within the scope of the inventive compounds, representative substituents, when R, $R_2$ or $R_5$ is a substituted $C_{(1-10)}$ alkyl, $C_{(2-10)}$ alkoxyl, $C_{(2-10)}$ alkenyl or $C_{(1-10)}$ hydroxyalkyl, may be:

amide, primary, secondary and tertiary amine, $C_{(2-8)}$ alkenyl, $C_{(1-8)}$ alkyl (including, e.g., branched and unbranched alkyl or alkenyl groups), $C_{(1-8)}$ alkoxyl, $C_{(1-8)}$ hydroxyalkyl, azide, carbonate, carbonyl, carboxylic acid, cyanide, $C_{(1-8)}$ haloalkyl (including, e.g., mono-, di- and tri-haloalkyl substituents, such as trihalomethyl), isocyanate, isothiocyanate, phosphate, phosphonate, primary, secondary or tertiary alcohol (including, e.g., any one of various diols, methanol, butanol, 1-cyclopentanol, ethanol, 2-ethyl-3-methyl-1-propanol, pentanol, propanol, and methylcyclohexanol), sulfonate, sulfone, sulfoxide, thioamide, thiocarbonate, thioester, thiolester, thiol, thiourea and urea.

The above-listed, substituents are also representative of substituents when $R_3$ or $R_4$ is a substituted $C_{(1-20)}$ alkyl, $C_{(1-20)}$ alkoxyl, $C_{(2-20)}$ alkenyl or $C_{(1-20)}$ hydroxyalkyl; R, $R_3$ or $R_5$ is a substituted carbocyclic or heterocyclic group; or $R_1$ is a substituted $CH_2$.

Representative R, $R_3$ or $R_5$ carbocyclic or heterocyclic groups may be, but are not limited to: anthracene, bicyclo[4.4.0]decane, bicyclo[2.2.1]heptane, bicyclo[3.2.0]heptane, bicyclo[4.1.0]heptane, bicyclo[2.2.1]hexane, bicyclo[4.3.0]nonane, bicyclo[2.2.2]octane, biphenyl, cyclopentadiene, cyclopentane, cyclobutane, cyclobutene, cycloheptane, cyclohexane, cyclooctane and cyclopropane, 1,2-diphenylethane, fluorene, indene, phenyl, quinone, terphenyl, napthalene, phenanthrene, terphenyl, toluene, xylene, azetidine, benzofuran, benzothiophene, carbazole, furan, glutarimide, indole, isoquinoline, lactam, lactone, oxazole, oxetane, oxirane, phthalimide, piperidine, pyrrolidine, pyran, pyridine, pyrrole, quinoline, tetrahydrofuran, tetrahydropyran, tetrahydrothiophene, thiophene, thymine, derivatives thereof and the like. Due primarily to availability and ease of synthesis, more preferred cyclic (carbocyclic or heterocyclic) groups include, but are not limited to, less complex ring systems, such as, for example, cyclopentane and cyclohexane, cyclopentadiene, phenyl, indene, toluene, xylene, furan, indole, thymine and xanthine.

A non-cyclic core moiety may include, but is not limited to, for example, acetamide, amide, amine, amino acid (one or two), carboxide, ester, terminal halogen or hydrogen atom, hydroxide, glutaric acid, glycine derivative, ketone, phosphate, phosphonate, sulfate, sulfonate, sulfone, sulfoxide, simple ionic functional group, thiol, thiolester or the like. Exemplary core moiety amino acids may include, but is limited to, one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be an amide, carboxyl ester, carboxide, hydrogen, hydroxide or a dipeptide comprising two amino acids selected from the foregoing exemplary list. A non-cyclic, halogen-core moiety may be, for example, bromine, chlorine, fluorine or iodine.

A cyclic core may be at least one five- to seven-member, non-heterocyclic (i.e. carbocyclic) ring or a heterocycle. The at least one five- to seven-membered cyclic core may preferably have from one to three, five- to six-membered ring structures in a predominantly planar configuration. An exemplary, non-heterocyclic ring core moiety may be selected from the group consisting of substituted or unsubstituted benzene; biphenyl; cyclohexane; cyclohexanedione; cyclopentanedione; napthlalene; phenol; quinone; salicylic acid; stilbene and tricyclododecane.

Although other heterocyclic cores are within the scope of the invention, the following representatives are preferred: substituted or unsubstituted barbituric acid; benzamide; lactam; glutarimide; homophthalimide; hydrophthalimide; imidazole; imidazole amide; indomethacin; isocarbostyril; lumazine; N-alkylheterocyclic; N-heterocyclic; pteridine; pthalimide; piperidine; pyridine; pyrimidine; pyrrole amide; quaternized N-heterocyclic; quinolizinedione; quinazolinone; quinoline; recorsinol; succinimide; theobromine; thymine; triazine; uric acid; uracil; vitamins A, E or K; or xanthine.

Representative substituents for the non-heterocyclic (i.e., carbocyclic) or heterocyclic core moieties include, for example, amide, primary, secondary and tertiary amine, $C_{(2-8)}$ alkenyl, $C_{(1-8)}$ alkyl (including, e.g., branched and unbranched alkyl or alkenyl groups), $C_{(1-8)}$ alkoxyalkyl, azide, carbonate, carbonyl, carboxylic acid, cyanide, $C_{(1-8)}$ haloalkyl (including, e.g., mono-, di- and tri-haloalkyl substituents, such as trihalomethyl), isocyanate, isothiocyanate, phosphate, phosphonate, primary, secondary or tertiary alcohol (including, e.g., any one of various diols, methanol, butanol, 1-cyclopentanol, ethanol, 2-ethyl-3-methyl-1-propanol, pentanol, propanol, and methylcyclohexanol), sulfonate, sulfone, sulfoxide, thioamide, thiocarbonate, thioester, thiolester, thiol, thiourea and urea.

Preferred non-heterocyclic ring cores include, but are not limited to, substituted or unsubstituted 1,3-cyclohexanedione, 1,3-cyclopentanedione; 1,3-dihydroxynaphthalene; or orthophenol.

Preferred heterocyclic cores include, but are not limited to, substituted or unsubstituted 3,7-dimethylxanthine, glutarimide, 3-methyl-7-pivoloylxanthine, methylthymine, methyluracil, 3-methylxanthine, tetrahydrophthalimide, thymine, uracil and xanthine, most preferably methyl-substituted xanthine. Exemplary preferred cores include, but are not limited to: $C_{(1-6)}$ alkyl-substituted thymine; $C_{(1-6)}$ alkyl-substituted uracil; 1,3-dihydroxynapthalene; 3,3-dimethylglutarimide; dihydrothymine; 2,4-dioxohexahydro-1,3,5-tetrazine; hexahydrophthalimide; homophthalimide; 2-hydroxypyridine; β-ionone as vitamin A methylbarbituric acid; 2,6,6-methyl-1-cyclohexene-1-acetaldehyde as vitamin A; methyldihydroxypyrazolopyrimidine, specifically, 1,3-dimethyldihydroxypyrazolo[4,3-d]pyrimidine;1-methyl-5,6-dihydrouracil; 1,7-dimethylxanthine, 3,7-dimethylxanthine; 7-methylhypoxanthine; 1-methyllumazine; 3-methyl-7-methylpivaloylxanthine; methylpyrrolopyrimidine; 1-methylpyrrolo [2,3-d] pyrimidine; 1-methyl-2,4(1H,3H)-quinolizinedione (1-methylbenzoyleneurea); methylthymine; 1-methyluracil; 3-methylxanthine; orotic acid; prostacyclin; 1-pyrrole amides; 2-pyrrole amides; 3-pyrrole amides; quinazolin-4(3H)-one; 1,2,3,4-tetrahydroisoquinoline; tetrahydrophthalimide; sulindac; uracil fused to naphthalene; 5- and/or 6-position substituted uracils (such as, for example, 5-bromouracil); tetralone to vitamin K; and 8-substituted xanthines (having substituents such as N or S).

Preferably, R is bonded to a nitrogen of the core moiety, if present, most preferably to the nitrogen of a glutarimide, methylthymine, thymine, uracil or xanthine core. In representative, preferred compounds, R having formula I may be bonded to an $N_1$ nitrogen of glutarimide; $N_1$ nitrogen of xanthine (and $N_3$ and $N_7$ xanthine nitrogens may be independently substituted by a member selected from the group consisting of hydrogen, $C_{(1-6)}$ alkyl, fluoro, chloro and amino); $N_3$ nitrogen of methylthymine; or $N_1$ nitrogen of uracil. Alternatively, R having formula I may be bonded to $N_1$ and $N_3$ xanthine nitrogens and $N_7$ xanthine nitrogen is substituted by a member selected from the group consisting of hydrogen, methyl, fluoro, chloro and amino. Representative, preferred inventive compounds are compounds of formulas II, III and IV:

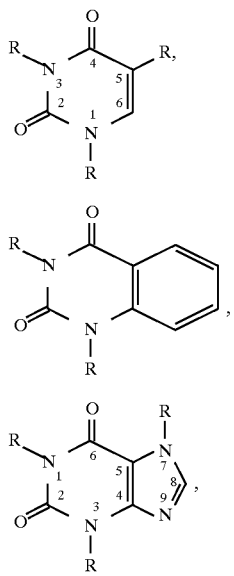

wherein R is defined above.

The invention also provides a pharmaceutical composition. Pharmaceutical compositions of the inventive compounds comprise a pharmaceutical carrier or diluent and some amount of an inventive compound. The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will, of course, depend upon the intended route of administration, for example, parenterally, topically, orally or by inhalation for treatment of a patient with disease symptoms. For topical administration, the pharmaceutical composition will be in the form of a cream, ointment, liniment, lotion, paste, aerosol or drop suitable for administration to the skin, eye, ear, lung or nose. For parenteral administration, the pharmaceutical composition will be in the form of a sterile injectable liquid. For oral administration, the pharmaceutical composition will be in the form of a tablet, capsule, powder, pellet, atroche, lozenge, syrup, liquid, emulsion or aqueous or non-aqueous liquid suspension.

The invention includes a method for treating an individual having a variety of diseases. The disease is characterized by or can be treated by inhibiting an immune response or a cellular response to external or in situ primary stimuli. Treatment of the disease states involves mediating the cellular response through a specific phospholipid-based second messenger pathway acting adjacent to a cell membrane inner leaflet. The second messenger pathway is activated in response to various noxious or proliferative stimuli, characteristic of disease states treatable using the inventive compounds or pharmaceutical compositions thereof. The inventive compounds are active by inhibiting various enzymes of this phospholipid second messenger pathway. The core moiety component of the inventive composition might serve to anchor the compound to an inner leaflet of a cell's plasma membrane allowing an "R" moiety of the inventive compound to interact with or inhibit an enzyme involved in phospholipid metabolism, usually leading to cellular accumulation of specific PA (phosphatidic acid) species.

More specifically, the invention includes methods for treating or preventing clinical symptoms of various disease states or reducing toxicity of other treatments by inhibiting cellular signaling through a second messenger pathway involving signaling through phosphatidic acid and through glycan phosphatidylinostinol (Gly PI).

Illustrative examples of compounds of the present invention include, but are not limited to, the following:

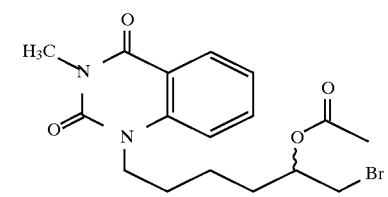

1205 1-(5-Acetoxy-6-bromohexyl)-3-methylbenzoyleneurea

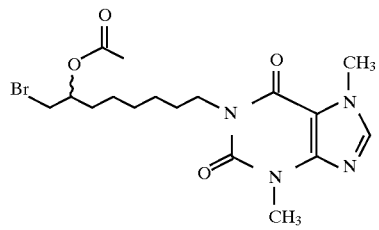

1514 1-(7-Acetoxy-8-bromooctyl)-3,7-dimethylxanthine

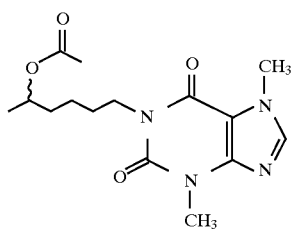
1515 1-(5-Acetoxyhexyl)-3,7-dimethylxanthine
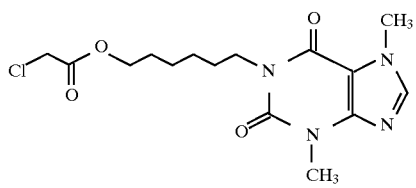
1527 1-[6-(Chloroacetoxy)hexyl]-3,7-dimethylxanthine
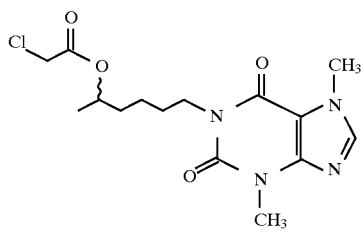
1529 1-[5-(chloroacetoxy)hexyl]-3,7-dimethylxanthine
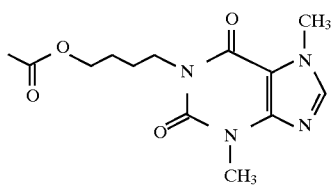
1543 1-(4-Acetoxybutyl)-3,7-dimethylxanthine
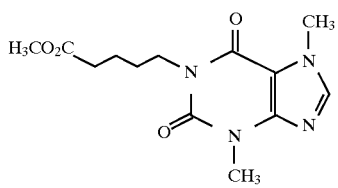
1554 1-(Pentoyl)-3,7-dimethylxanthine carboxylic acid methyl ester
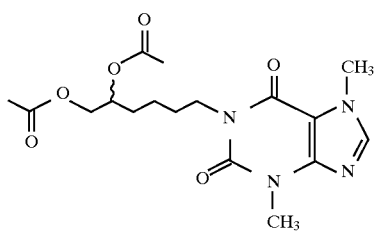
1572 1-(5,6-Diacetoxyhexyl)-3,7-dimethylxanthine

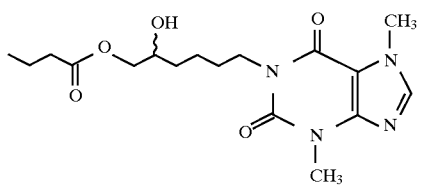
1576 1-(6-Butyroxy-5-hydroxyhexyl)-3,7-dimethylxanthine
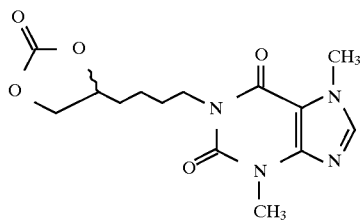
1578 1-(5,6-Carbonyldioxyhexyl)-3,7-dimethylxanthine
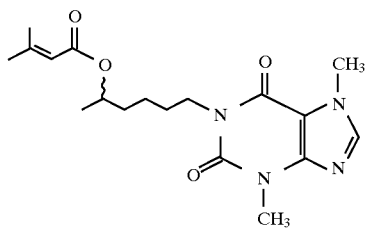
1579 1-([5-(3-Methyl-2-butenoyl)]hexyl-3,7-dimethylxanthine
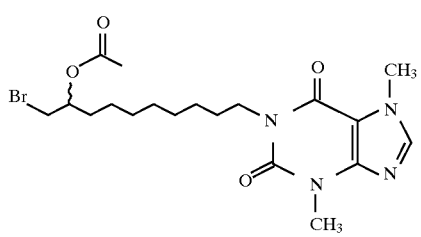
1583 1-(9-Acetoxy-10-bromodecyl)-3,7-dimethylxanthine
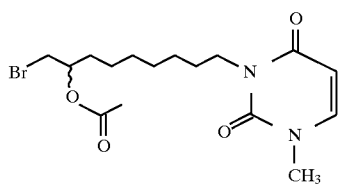
1801 3-(8-Axetoxy-9-bromononyl)-1-methyluracil
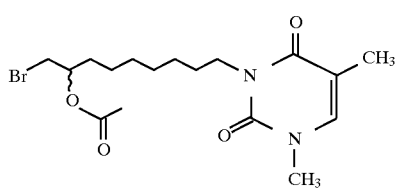
1908 3-(8-Acetoxy-9-bromononyl)-1-methylthymine

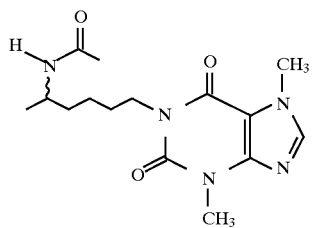
2538 1-(5-Acetamidohexyl)-3,7-dimethylxanthine
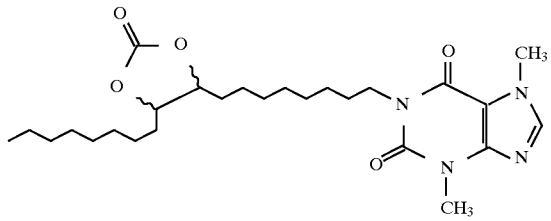
3508 1-(9,10-Carbonyldioxyoctadecyl)-3,7-dimethylxanthine
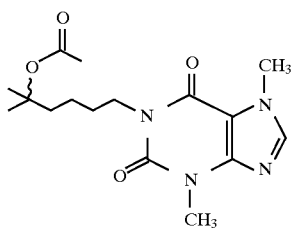
3523 1-(5-Acetoxy-4-methylpentyl)-3,7-dimethylxanthine
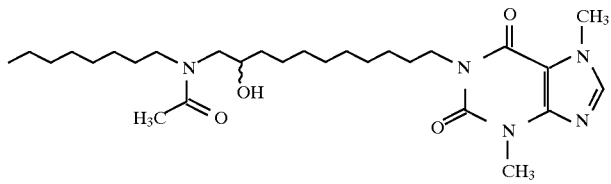
3532 1-[11-(N-Ocylacetamido)-10-hydroxyundecyl]-3,7-dimethylxanthine
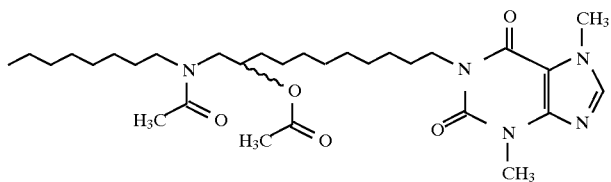
3537 1-[11-(N-Octylacetamido)-10-acetoxyundecyl)]-3,7-dimethylxanthine
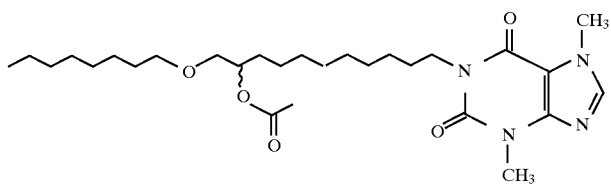
3541 1-(11-Octoxy-10-acetoxyundecyl)-3,7-dimethylxanthine

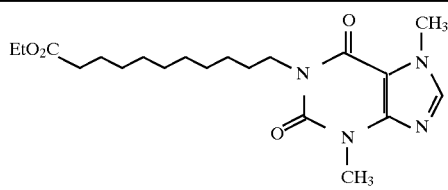
3542 1-(Ethyl-11-yl-undecanoate)-3,7-dimethylxanthine
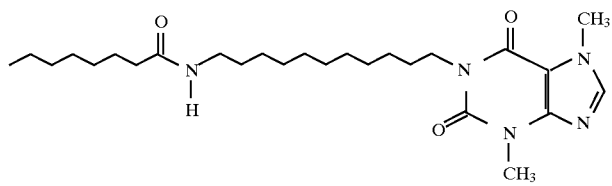
3546 1-(11-Octanoamido)undecyl)-3,7-dimethylxanthine
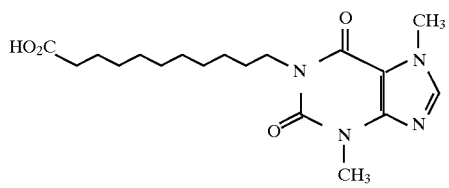
3549 1-[11-yl-Undecanoic acid]-3,7-dimethylxanthine
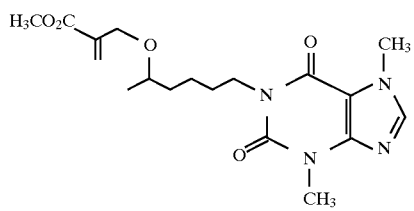
3551 1-(5R-(2-Carbomethoxyallyloxy)hexyl)-3,7-dimethylxanthine
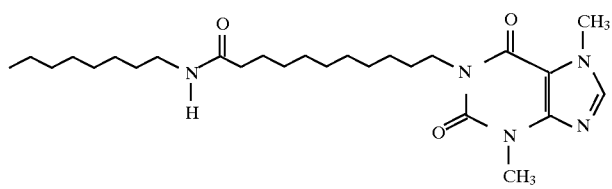
3554 1-(N-Ocyl-11-yl-undecanamide)-3,7-dimethylxanthine
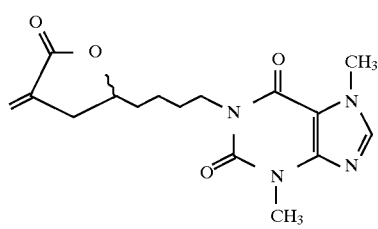
3557 1-(5-hydroxy-7-carboxy-7-octenyl)-3,7-dimethylxanthine-γ-lactone
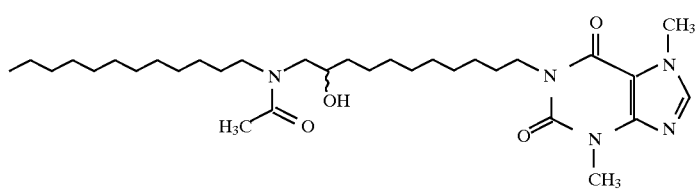

-continued 3559 1-[11-(N-Dodecylacetoamido)-10-hydroxyundecyl]-3,-dimethylxanthine

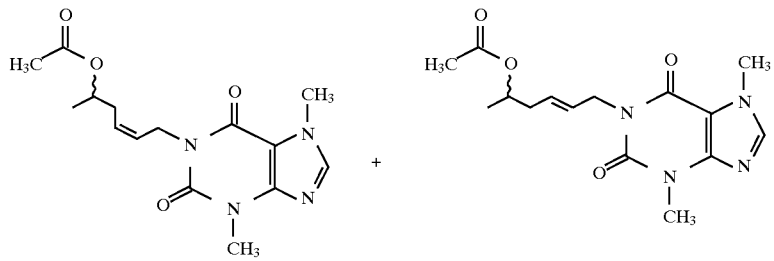

3560 1-[5-Acetoxyhex-3-enyl]-3,7-dimethylxanthine

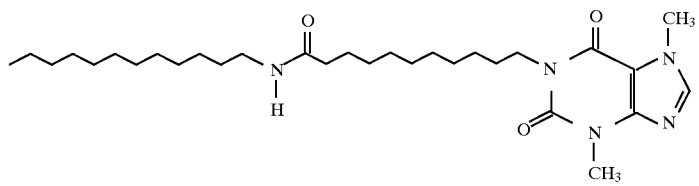

3562 1-(N-Dodecyl-11-yl-undecanamide)-3,7-dimethylxanthine

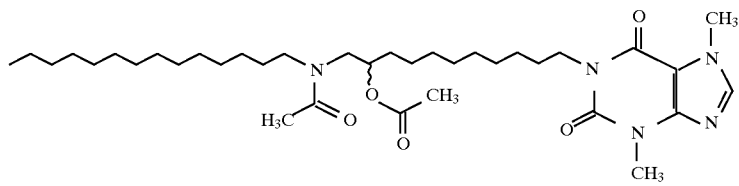

3564 1-[11-(N-Tetradecylacetamido)-10-acetoxyundecyl]-3,7-dimethylxanthine

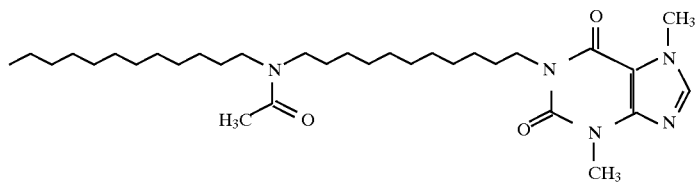

3565 1-[11-(N-Dodecylacetamido)undecyl]-3,7-dimethylxanthine

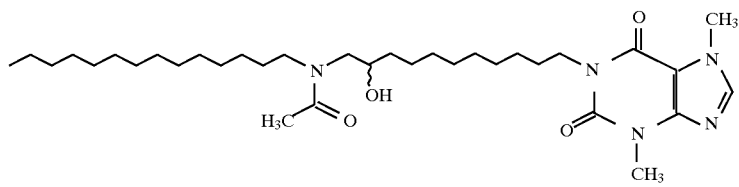

3569 1-[11-(N-Tetradecylacetamido)-10-hydroxyundecyl]-3,7-dimethylxanthine

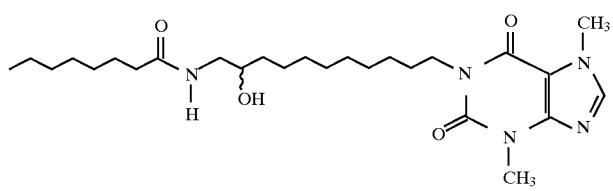

3570 1-[11-Octanoamido-10-hydroxyundecyl)-3,7-dimethylxanthine

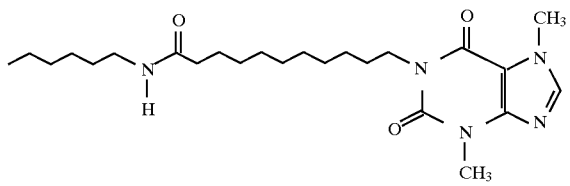

3571 1-(N-Hexyl-11-yl-undecanamide)-3,7-dimethylxanthine

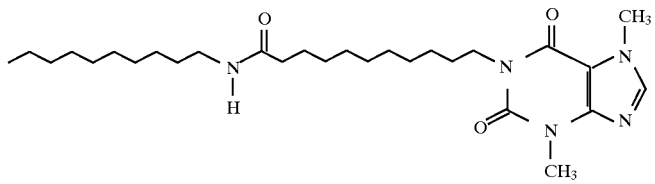

3572 1-(N-Decyl-11-yl-undecanamide)-3,7-dimethylxanthine

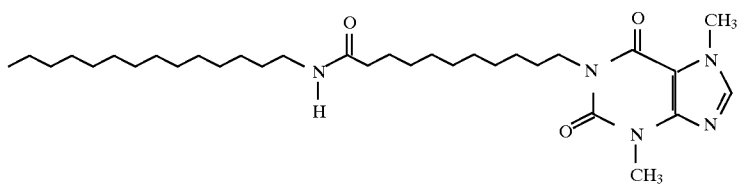

3573 1-(N-Tetradecyl-11-yl-undecanamide)-3,7-dimethylxanthine

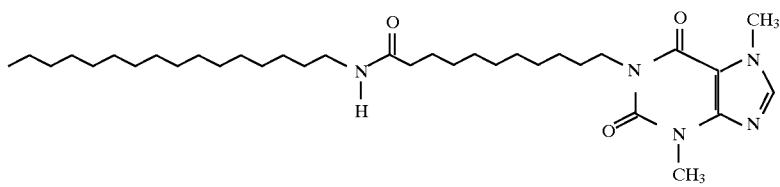

3574 1-[N-Hexadecyl-11-yl-undecanamide)-3,7-dimethylxanthine

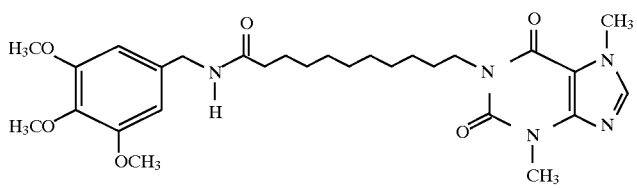

3577 1-[N-(3,4,5-Trimethoxybenzyl)-11-yl-undecanamide]-3,7-dimethylxanthine

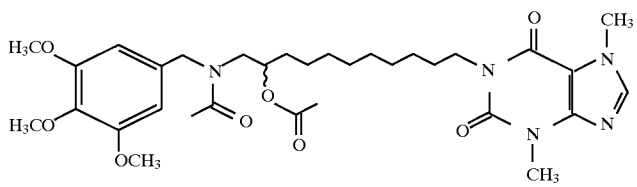

3586 1-[11-(3,4,5-Trimethoxybenzylacetamido)-10-acetoxyundecyl]-3,7-dimethylxanthine

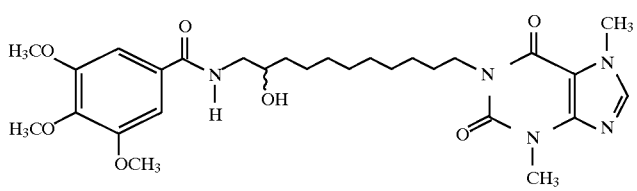

3588 1-[11-(3,4,5-Trimethoxybenzamido)-10-hydroxyundecyl]-3,7-dimethylxanthine

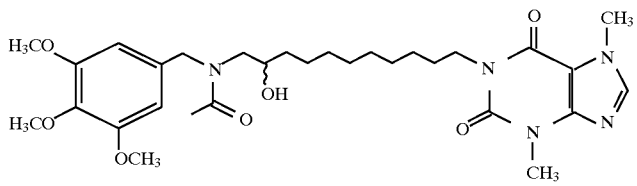

3589 1-[11-(3,4,5-Trimethoxybenzylacetamido)-10-hydroxyundecyl]-3,7-dimethylxanthine

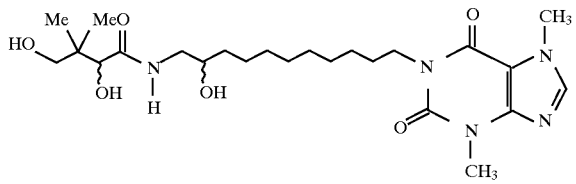

3592 1-[11-Pantothenic acid amido-10-hydroxyundecyl]-3,7-dimethylxanthine

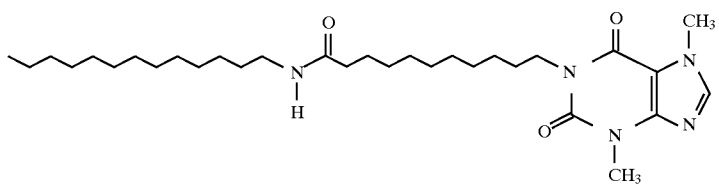

3598 1-(N-Tridecyl-11-yl-undecanamide)-3,7-dimethylxanthine

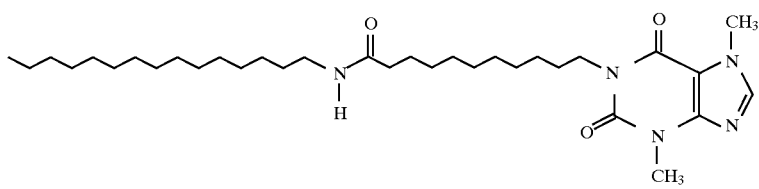

3599 1-(N-Pentadecyl-11-yl-undecanamide)-3,7-dimethylxanthine

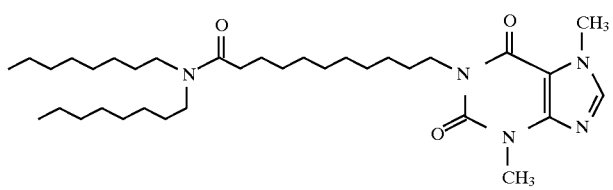

4503 1-[N,N-Dioctyl-11-yl-undecanamide)-3,7-dimethylxanthine

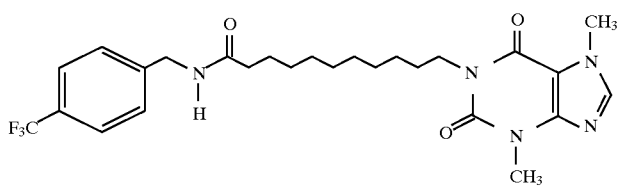

4504 1-[N-(4-Trifluoromethylbenzyl)-11-yl-undecanamide]-3,7-dimethylxanthine

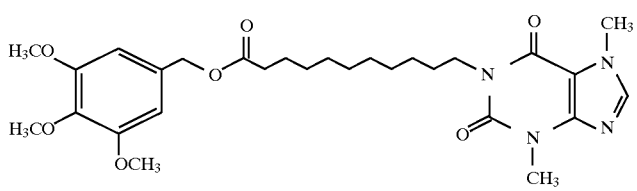

4511 1-(3,4,5-Trimethoxybenzyl 11-yl-undecanoate)-3,7-dimethylxanthine

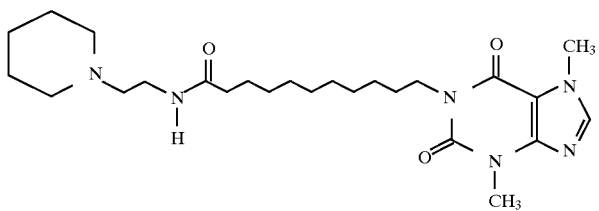
4512  1-[N-(2-Piperidinoethyl)-11-yl-undecanamide)-3,7-dimethylxanthine
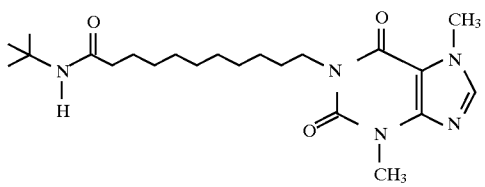
4518  1-[(N-tert-Butyl)-11-yl-undecanamide]-3,7-dimethylxanthine
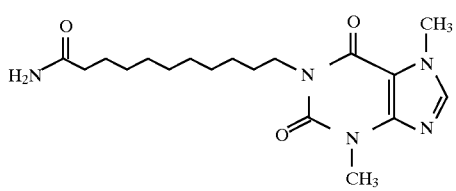
4519  1-(11-yl-Undecanamide)-3,7-dimethylxanthine
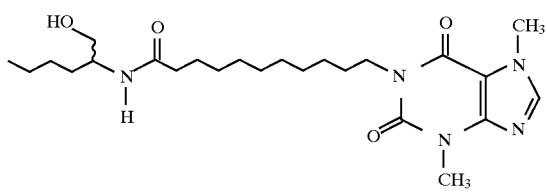
4520  1-[N-(1-Hydroxymethyl)pentyl-11-yl-undecanamide]-3,7-dimethylxanthine
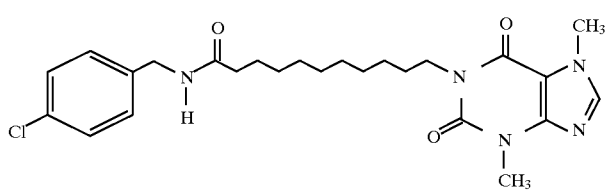
4523  1-[N-(4-Chlorobenzyl)-11-yl-undecanamide]-3,7-dimethylxanthine
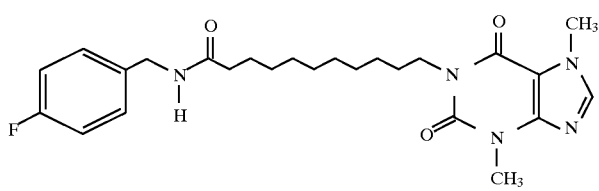
4524  1-[N-(4-Fluorobenzyl)-11-yl-undecanamide]-3,7-dimethylxanthine
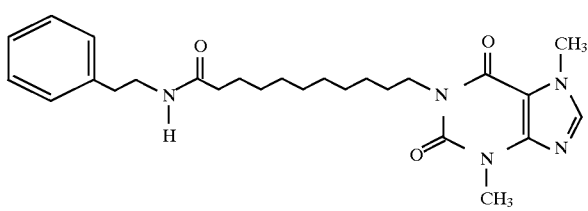
4525  1-[N-(Phenethyl)-11-yl-undecanamide]-3,7-dimethylxanthine

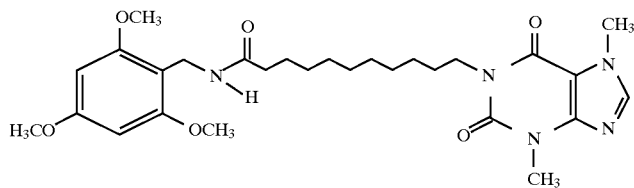
4526 1-[N-(2,4,6-Trimethoxybenzyl)-11-yl-undecanamide]-3,7-dimethylxanthine
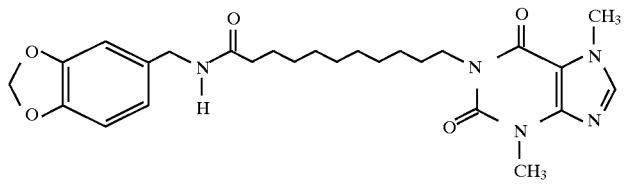
4533 1-[N-(Piperonyl)-11-yl-undecanamide]-3,7-dimethylxanthine
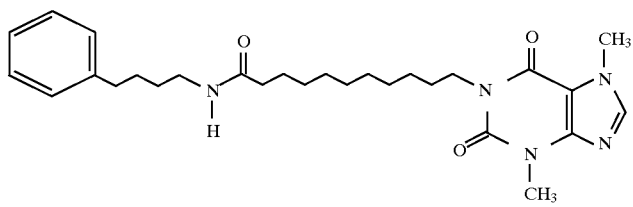
4534 1-[N-(4-Phenylbutyl)-11-yl-undecanamide]-3,7-dimethylxanthine
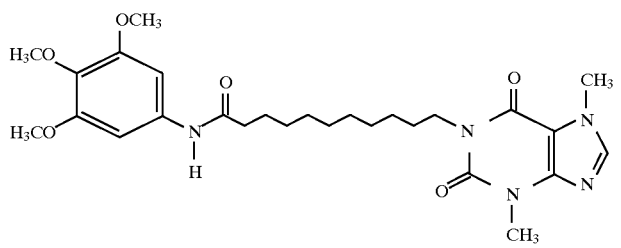
4535 1-[N-3,4,5-Trimethoxyphenyl)-11-yl-undecanamide]-3,7-dimethylxanthine
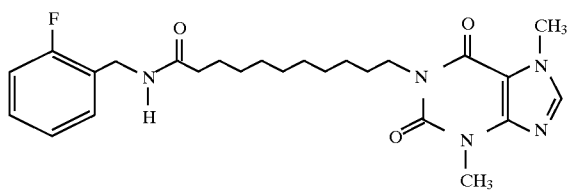
4536 1-[N-(2-Fluorobenzyl)-11-yl-undecanamide]-3,7-dimethylxanthine
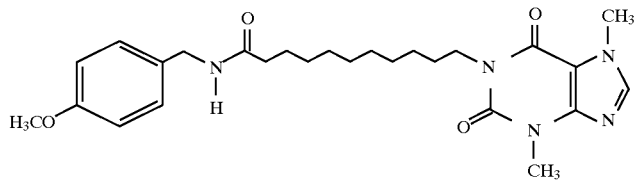
4537 1-[N-(4-methoxybenzyl)-11-yl-undecanamide]-3,7-dimethylxanthine

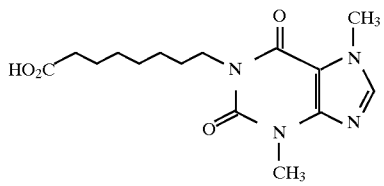
4538 1-(8-yl-Octanoic acid)-3,7-dimethylxanthine
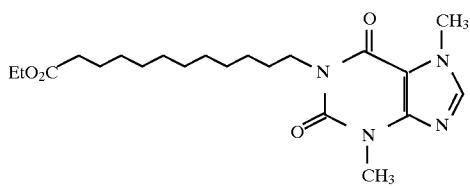
4550 1-(Ethyl 12-yl-dodecanoate)-3,7-dimethylxanthine
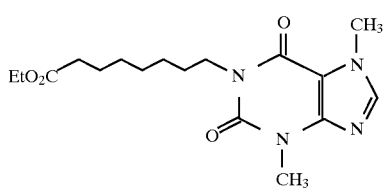
4551 1-(Ethyl-8-yl-octanoate)-3,7-dimethylxanthine
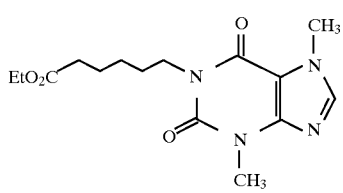
4552 1-(Ethyl 6-yl-hexanoate)-3,7-dimethylxanthine
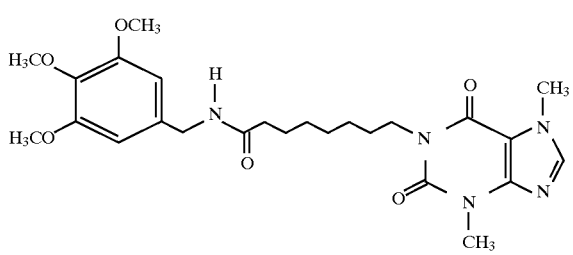
4553 1-[N-(3,4,5-Trimethoxybenzyl)-8-yl-octanamide]-3,7-dimethylxanthine
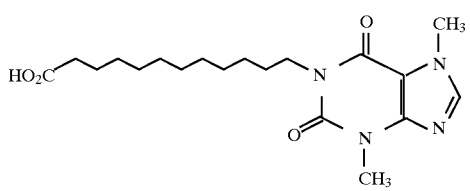
4555 1-(12-yl-Dodecanoic acid)-3,7-dimethylxanthine
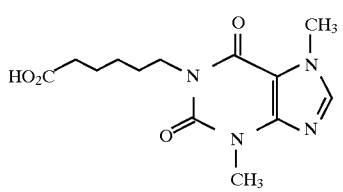

4556 1-(6-yl-Hexanoic acid)-3,7-dimethylxanthine
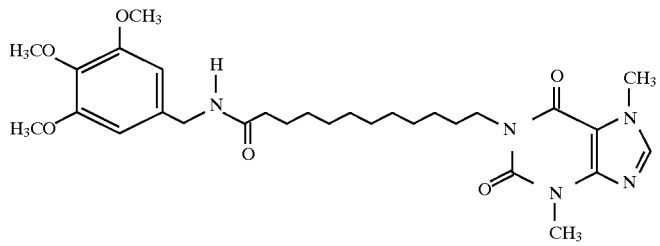
4557 1-[N-(3,4,5-Trimethoxybenzyl)-12-yl-dodecanamide]-3,7-dimethylxanthine
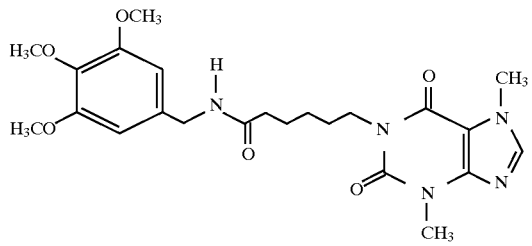
4558 1-[N-(3,4,5-Trimethoxybenzyl)-6-yl-hexanamide]-3,7-dimethylxanthine
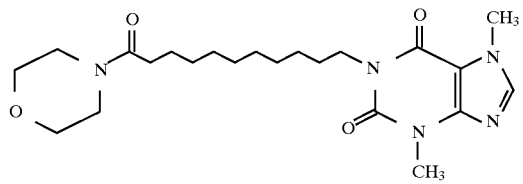
4559 1-[N-(Morpholine)-11-yl-undecanoamide]-3,7-dimethylxanthine
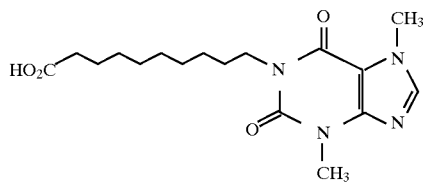
4563 1-(10-yl-Decanoic acid)-3,7-dimethylxanthine
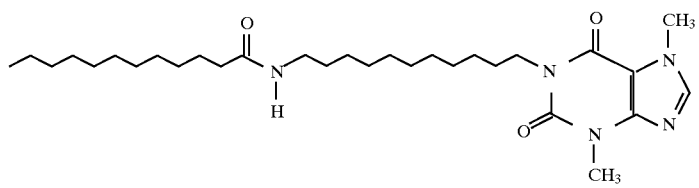
4564 1-[11-(Dodecamido)undecyl]-3,7-dimethylxanthine
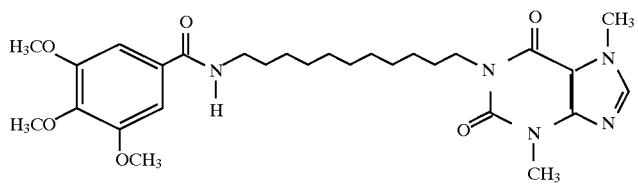
4565 1-[11-(3,4,5-Trimethoxybenzamido)undecyl]-3,7-dimethylxanthine

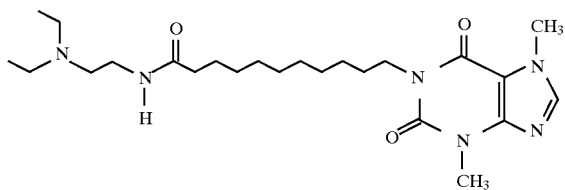

4566  1-[N-(2-N',N'-Diethylaminoethyl)-11-yl-undecanamide]-3,7-dimethylxanthine

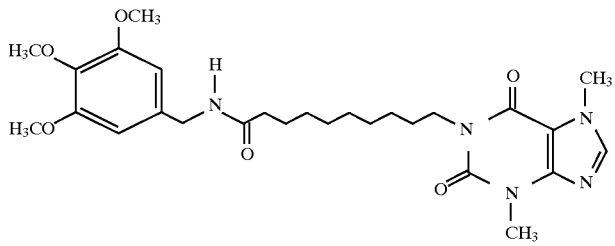

4567  1-[N-(3,4,5-Trimethoxybenzyl)-10-yl-decanamide]-3,7-dimethylxanthine

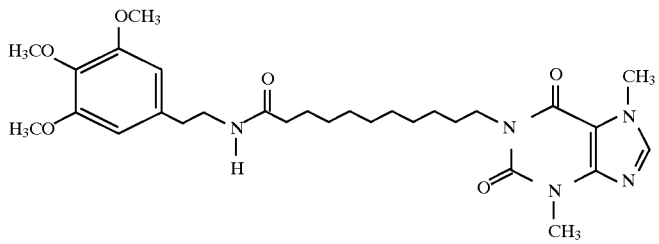

4579  1-[N-(3,4,5-Trimethoxyphenethyl)-11-yl-undecanamide]-3,7-dimethylxanthine

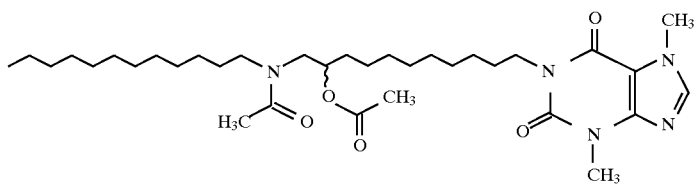

4584  1-[11-(N-Dodecylacetamido)-10-acetoxyundecyl]-3,7-dimethylxanthine

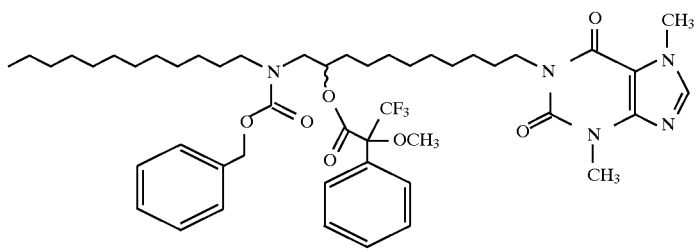

4586  1-[11-Dodecylamino(N-benzyloxycarbonyl)-10-(α-methoxy-α-trifluromethyl)-
phenylacetoxy)-undecyl]-3,7-dimethylxanthine

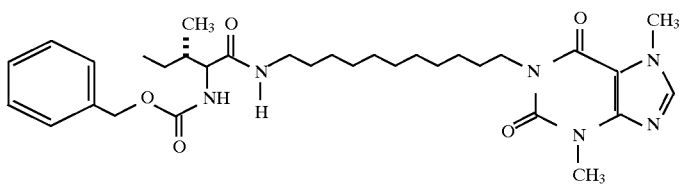

4587  1-[N-(N-carbobenzyloxy isoleucine)-11-yl-undecanoamide]-3,7-dimethylxanthine

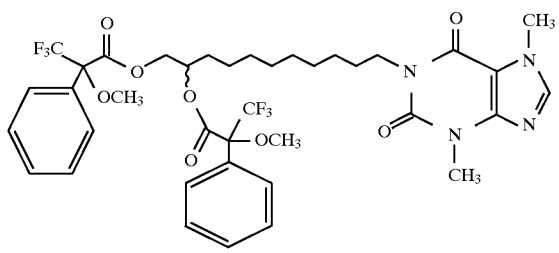

4588 1-[11,10-di(α-methoxy-α-(trifluoromethyl)phenylacetoxy)undecyl]-3,7-dimethylxanthine

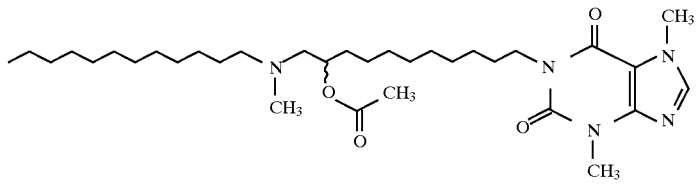

4589 1-[11-(N-Methyl-N-dodecylamino)-10-acetoxyundecyl]-3,7-dimethylxanthine

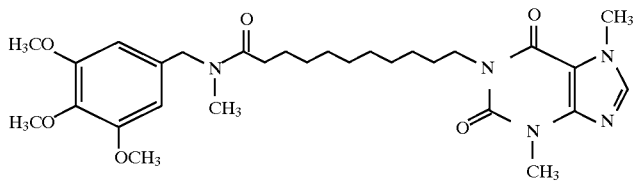

4590 1-[N-Methyl-N-(3,4,5-trimethoxybenzyl)-11-yl-undecanamide]-3,7-dimethylxanthine

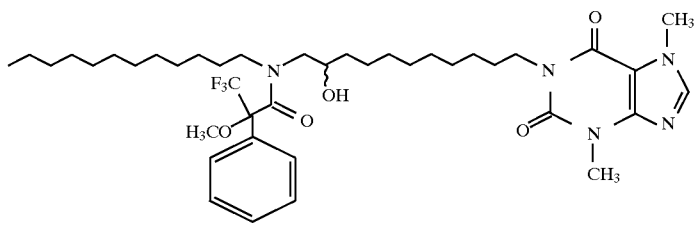

4591 1-{11-[N-Dodecyl(R)-2-methoxy-2-phenylacetamido]-10-hydroxyundecyl}-3,7-dimethylxanthine

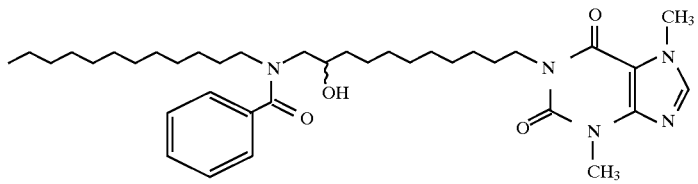

4594 1-[11-(Dodecyl benzamido)-10-hydroxyundecyl]-3,7-dimethylxanthine

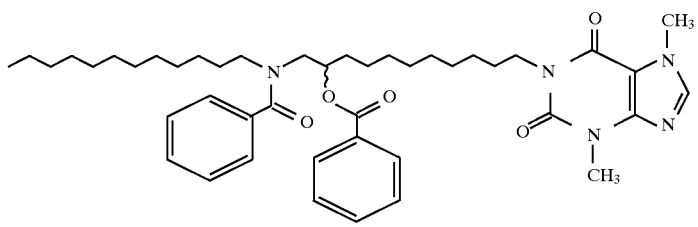

4599 1-[11-(N-Dodecyl benzamido)-10-benzoylundecyl]-3,7-dimethylxanthine

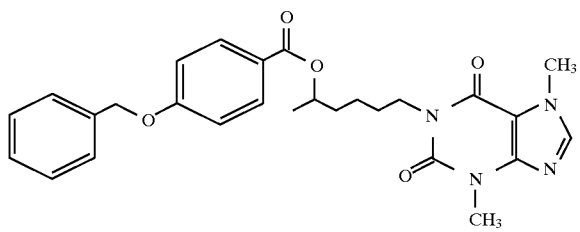

5505 R-1-(5-(4'-benzyloxybenzoyloxy)hexyl)-3,7-dimethylxanthine

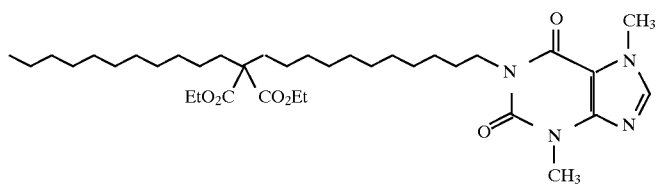

5509 1-[12,12-bis(Ethoxycarbonyl)tricosanyl]-3,7-dimethylxanthine

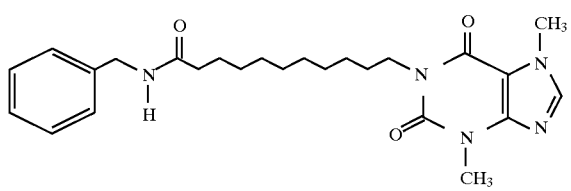

5513 1-[N-(Benzyl)-11-yl-undecanoamide]-3,7-dimethylxanthine

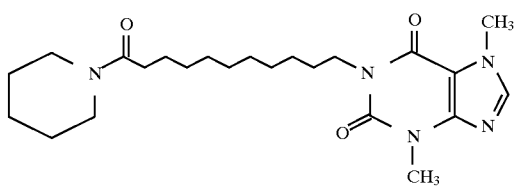

5514 1-[N-(Piperidinyl)-11-yl-undecanoamide]-3,7-dimethylxanthine

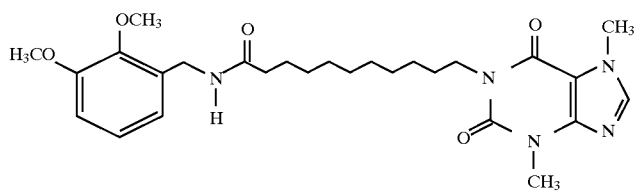

5515 1-[N-(2,3-Dimethoxybenzyl)-11-yl-undecanoamide]-3,7-dimethylxanthine

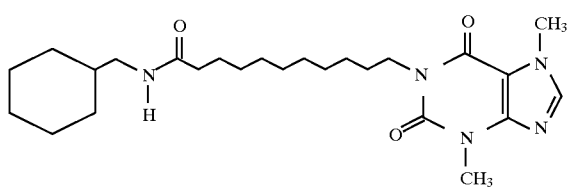

5516 1-[N-(Cyclohexylmethyl)-11-yl-undecanoamide]-3,7-dimethylxanthine

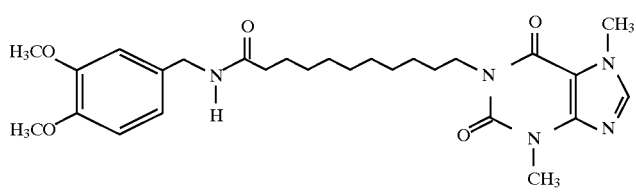

5517 1-[N-(3,4-Dimethoxybenzyl)-11-yl-undecanoamide]-3,7-dimethylxanthine

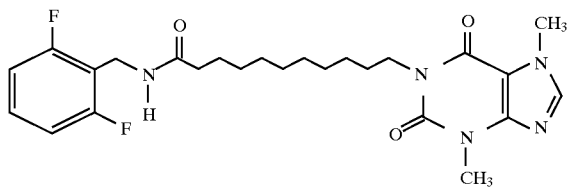

5518 1-[N-(2,6-Difluorobenzyl)-11-yl-undecanoamide]-3,7-dimethylxanthine

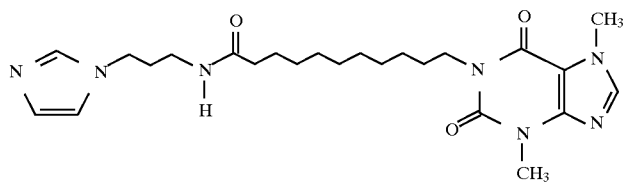

5519 1-[N-(3-Imidazolopropyl)-11-yl-undecanoamide]-3,7-dimethylxanthine

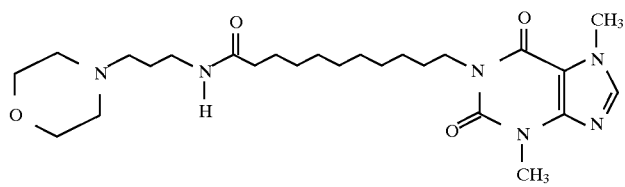

5520 1-[N-(3-Morpholinopropyl)-11-yl-undecanoamide]-3,7-dimethylxanthine

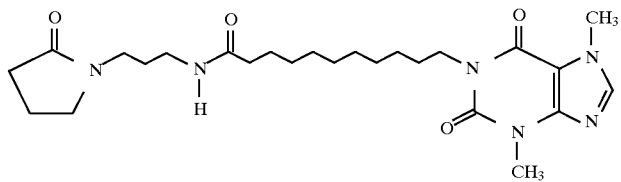

5521 1-[N-(3-Pyrrolidinonylpropyl)-11-yl-undecanoamide]-3,7-dimethylxanthine

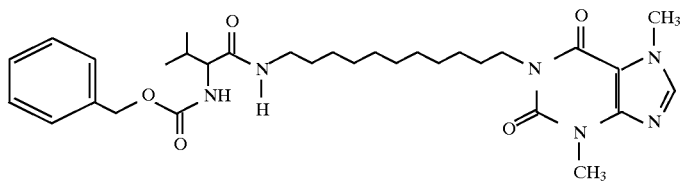

5523 1-[11-(2-Carbobenzyloxyamino-3-methylbutyronamido)undecyl]-3,7-dimethylxanthine

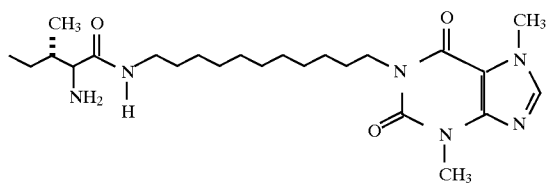

5524 1-[11-(2-Amino-3-methylpentanamido)undecyl]-3,7-dimethylxanthine

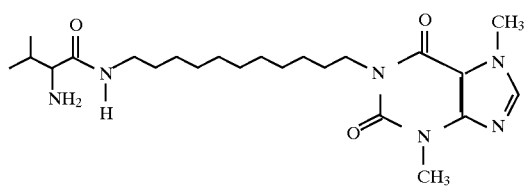

5525 1-[11-(2-Amino-3-methylbutyronamido)undecyl]-3,7-dimethylxanthine

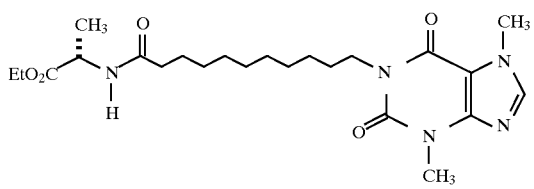

5526 1-[11-(1-Ethoxycarbonylethylamino)-11-oxoundecyl]-3,7-dimethylxanthine

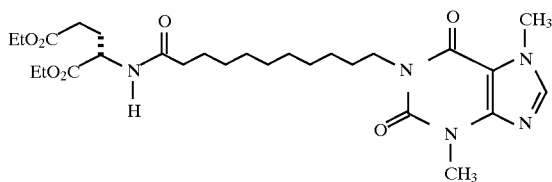

5529 1-(11-[1,3-Bis(ethoxycarbonyl)propylamino]-11-oxoundecyl)-3,7-dimethylxanthine

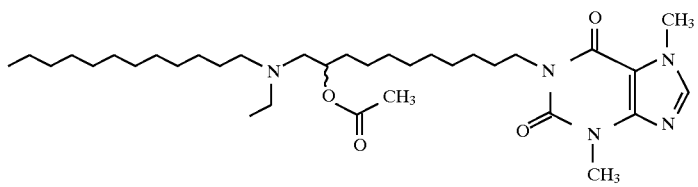

5532 1-(11-Dodecylethylamino-10-acetoxyundecyl)-3,7-dimethylxanthine

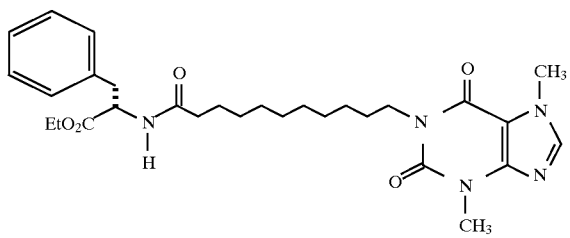

5533 1-[11-(1-Ethoxycarbonyl-2-phenylethylamino)-11-oxoundecyl]-3,7-dimethylxanthine

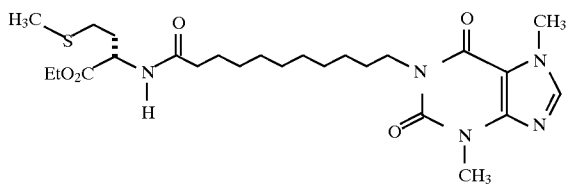

5534 1-[11-(1-Ethoxycarbonyl-3-methylthiopropylamino)-11-oxoundecyl]-3,7-dimethylxanthine

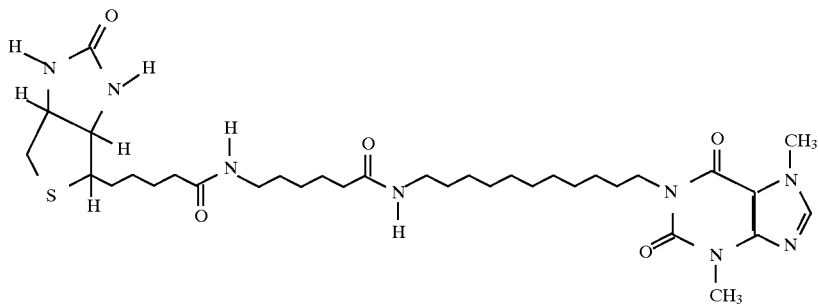

5535 1-(11-Biotinylamidoundecyl)-3,7-dimethylxanthine

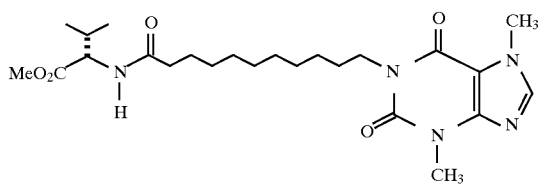

5543 1-[11-(1-Methoxycarbonyl-2-Methylpropylamino)-11-oxoundecyl]-3,7-dimethylxanthine

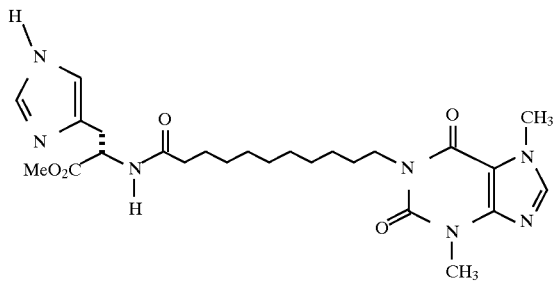

5544 1-[11-(2-[5-Imidazolyl]-1-methoxycarbonylethylamino)-11-oxoundecyl]]-3,7-dimethylxanthine

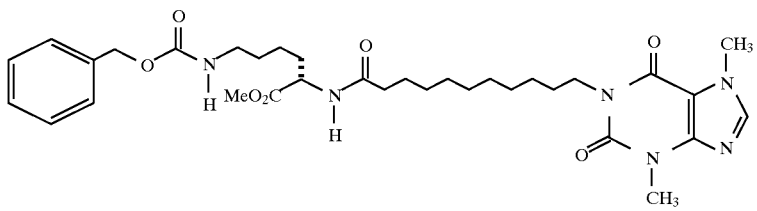

5545 1-[11-(5-Carbobenzyloxyamino-1-methoxycarbonylpentylamino)-11-oxoundecyl]-3,7-dimethylxanthine

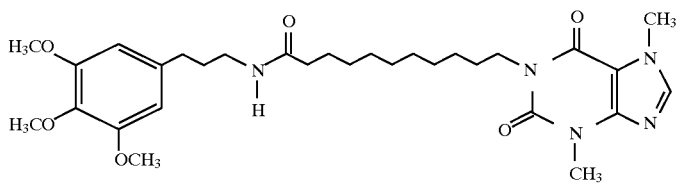

5546 1-(N-[3-(3,4,5-Trimethoxyphenyl)propyl]-11-yl-undecanamide)-3,7-dimethylxanthine

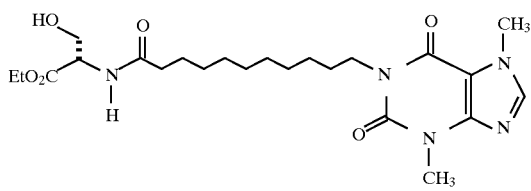

5547 1-[11-(1-Ethoxycarbonyl-2-hydroxyethylamino)-11-oxoundecyl]-3,7-dimethylxanthine

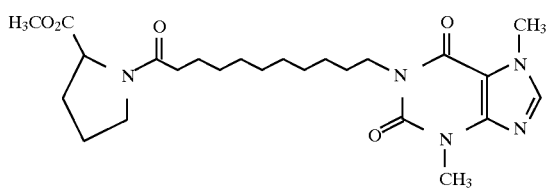

5548 1-[11-(2-Methoxycarbonylpyrrolidin-1-yl)-11-oxoundecyl]-3,7-dimethylxanthine

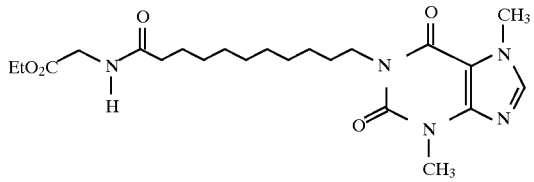

5552 1-[11-(Ethoxycarbonylmethylamino)-11-oxoundecyl]-3,7-dimethylxanthine

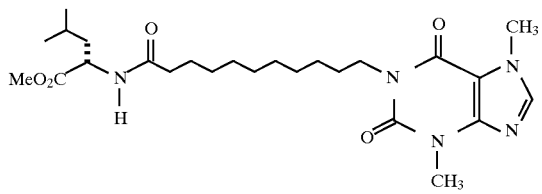

5553 1-[11-(1-Methoxycarbonyl-3-methylbutylamino)-11-oxoundecyl]-3,7-dimethylxanthine

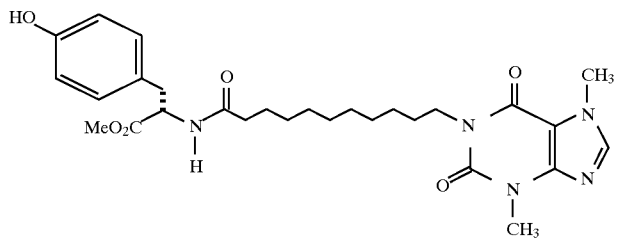

5554 1-(11-[1-Methoxycarbonyl-2-(4-hydroxyphenyl)ethylamino]-11-oxoundecyl)-3,7-dimethylxanthine

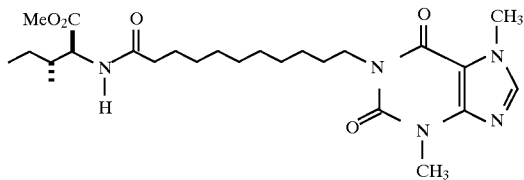

5555 1-[11-(1-Methoxycarbonyl-2-methylbutylamino)-11-oxoundecyl]-3,7-dimethylxanthine

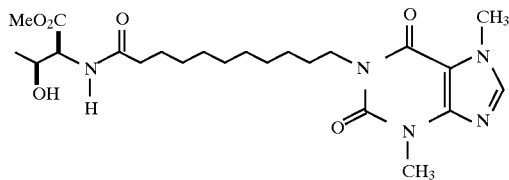

5556 1-[11-(2-Hydroxy-1-methoxycarbonylpropylamino)-11-oxoundecyl]-3,7-dimethylxanthine

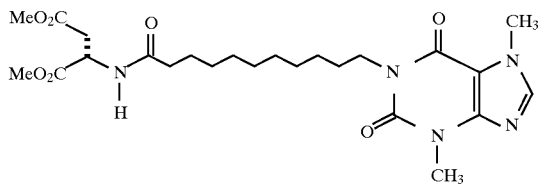

5557 1-(11-[1,2-Bis(methoxycarbonyl)ethylamino]-11-oxoundecyl)-3,7-dimethylxanthine

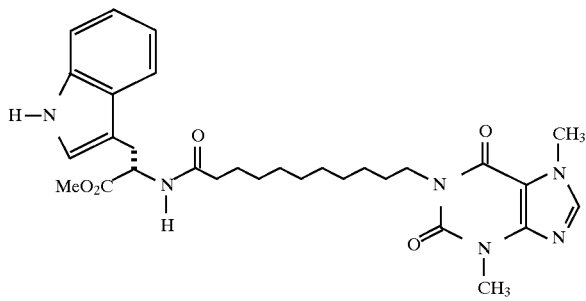

5559 1-(11-[2-(3-Indolyl)-1-methoxycarbonylethylamino]-11-oxoundecyl)-3,7-dimethylxanthine

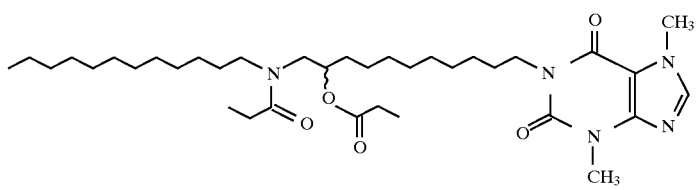

5560 1-[11-(N-Dodecyl propionamido)-10-propionylundecyl]-3,7-dimethylxanthine

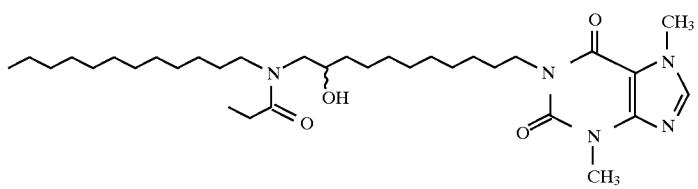

5563 1-[11-(N-Dodecyl propionamido)-10-hydroxyundecyl]-3,7-dimethylxanthine

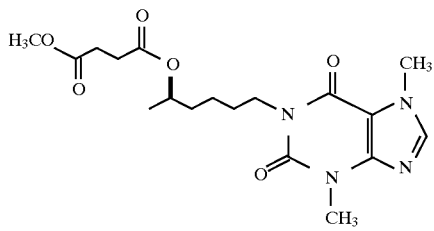

5565 R-1-(5-Hydroxy)hexyl)-3,7-dimethylxanthine methyl succinate

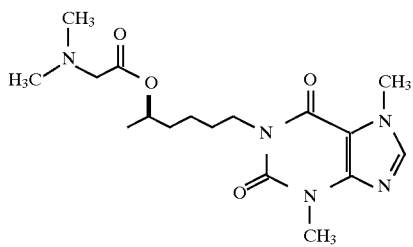

5566 R-1-(5-Hydroxy)hexyl)-3,7-dimethylxanthine N,N-dimethylglycinate

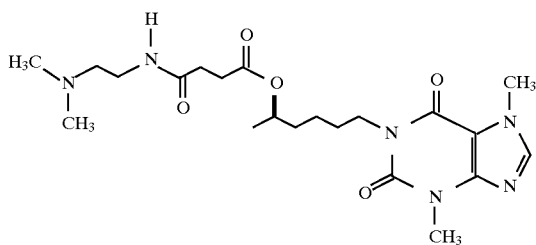

5567 R-1-(5-[[2-(Dimethylamino)ethyl]amino]-1,4-dioxobutyl]oxy)hexyl)-3,7-dimethylxanthine

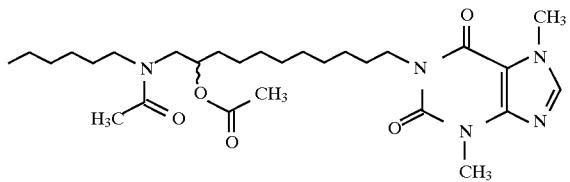
5569 1-[11-(N-Hexylacetamido-10-acetoxyundecyl]-3,7-dimethylxanthine
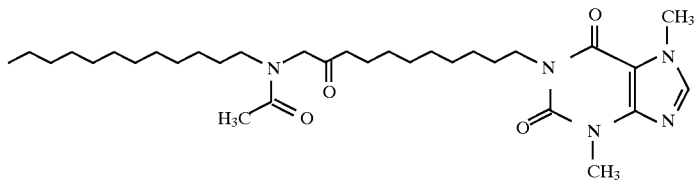
5570 1-(11-[N-Dodecylacetamido]-10-oxoundecyl}-3,7-dimethylxanthine
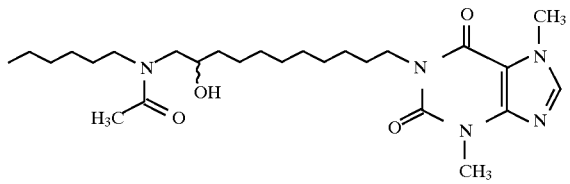
5572 1-[11-(N-Hexylacetamido)-10-hydroxyundecyl]-3,7-dimethylxanthine
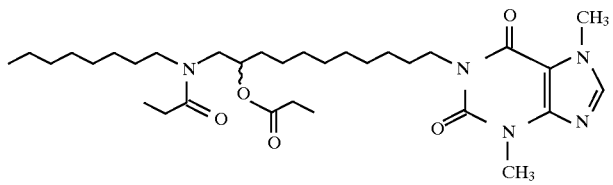
5576 1-[11-(N-Octyl propionamido)-10-propionoxyundecyl]-3,7-dimethylxanthine
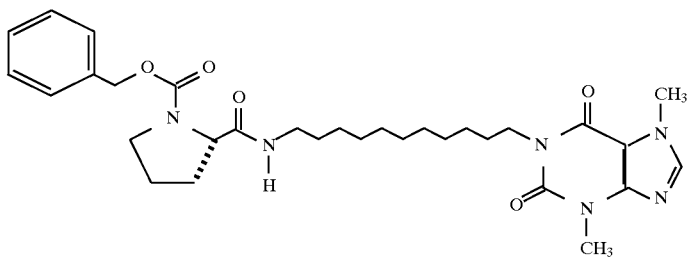
5577 1-[11-(1-Carbobenzyloxypyrrolidin-2-yl-formamido)undecyl]-3,7-dimethylxanthine
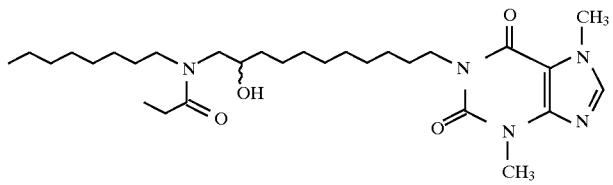
5578 1-[11-(N-Octyl propionamido)-10-hydroxyundecyl]-3,7-dimethylxanthine

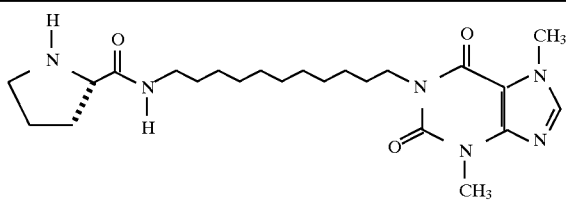
5580 1-[11-(Pyrrolidin-2-yl-formamido)undecyl]-3,7-dimethylxanthine
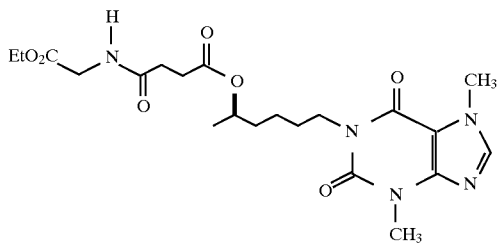
5584 R-1-(5-Hydroxyhexyl)-3,7-dimethylxanthine ethyl glycinyl succinate
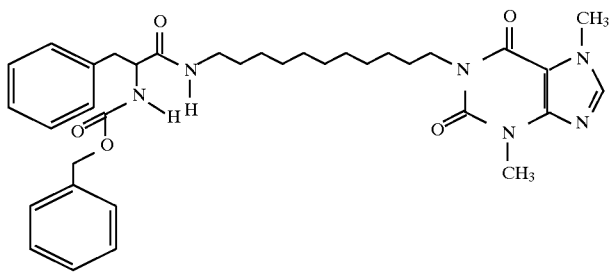
5586 (S)-1-[11-(2-Carbobenzyloxyamino-3-phenylpropionamido)undecyl]-3,7-dimethylxanthine
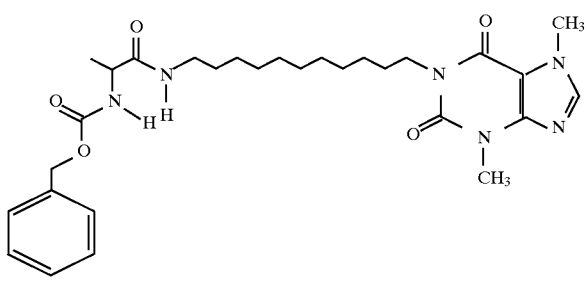
5587 (S)-1-[11-(2-Carbobenzyloxyaminopropionamido)undecyl]-3,7-dimethylxanthine
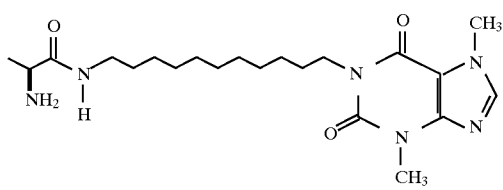
5588 (S)-1-[11-(2-Aminopropionamido)undecyl]-3,7-dimethylxanthine
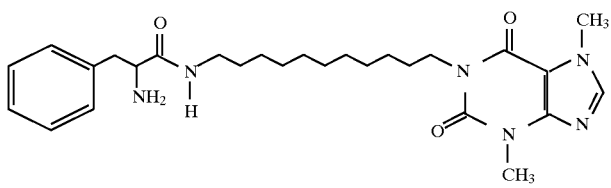
5591 (S)-1-[11-(2-Amino-3-phenylpropionamido)undecyl]-3,7-dimethylxanthine

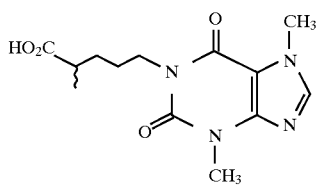
5593 1-(4-Methyl-5-yl-pentanoic acid)-3,7-dimethylxanthine
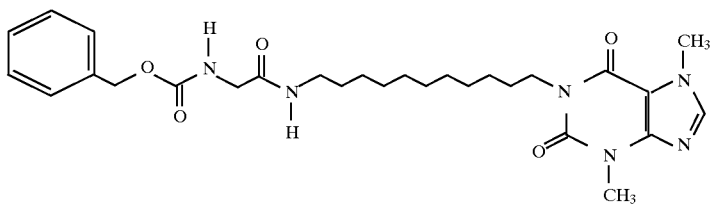
5595 1-[11-(Carbobenzyloxyaminoacetamido)undecyl]-3,7-dimethylxanthine
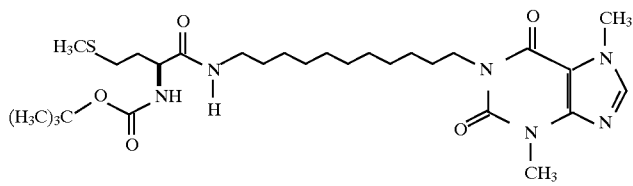
5596 (S)-1-[11-(2-Carbobutoxyamino-4-methylthiobutyronamido)undecyl]-3,7-dimethylxanthine
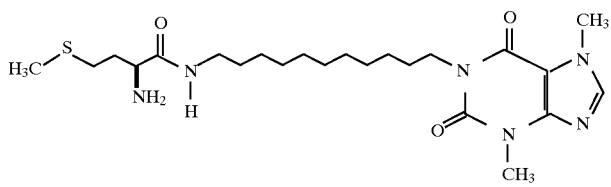
5599 (S)-1-[11-(2-Amino-4-methylthiobutryonamido)undecyl]-3,7-dimethylxanthine
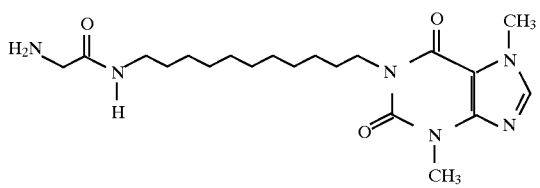
6500 1-[11-(Aminoacetamido)undecyl]-3,7-dimethylxanthine
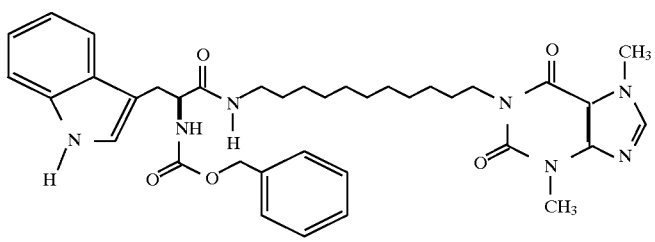
6506 1-(11-[2-Carbobenzyloxyamino-3-(3-indolyl)propionamido]undecyl)-3,7-dimethylxanthine

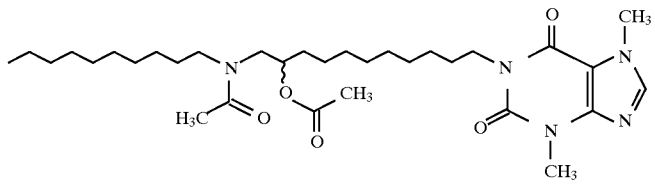

6508 1-[11-(N-carbobenzyloxyleucine)amidoundecyl]-3,7-dimethylxanthine

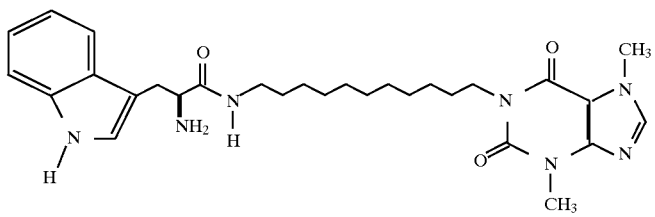

6509 1-[11-(N-Decylacetamido)-10-acetoxyundecyl]-3,7-dimethylxanthine

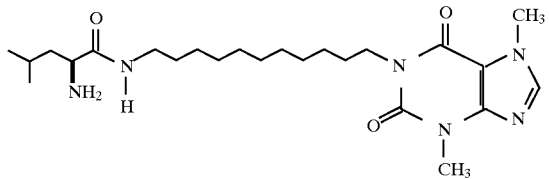

6511 1-(11-[2-Amino-3-(3-indolyl)propionamido]undecyl)-3,7-dimethylxanthine

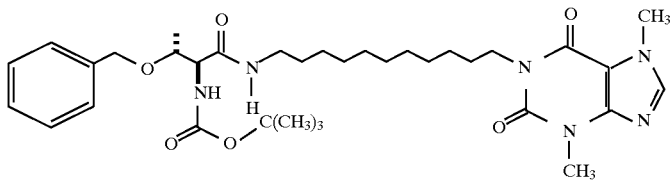

6512 1-[11-(2-Amino-4-methylpentanamido)undecyl]-3,7-dimethylxanthine

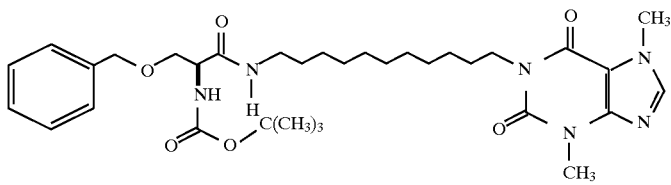

6516 (S)-1-[11-(2-Carbobutoxyamino-3-benzyloxybutyronamido)undecyl]-3,7-dimethylxanthine

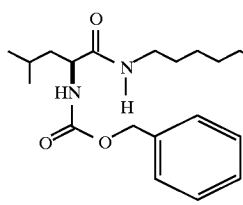 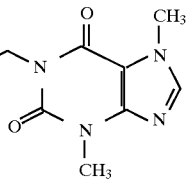

6517 (S)-1-[11-(2-Carbobutoxyamino-3-benzyloxypropionamido)undecyl]-3,7-dimethylxanthine

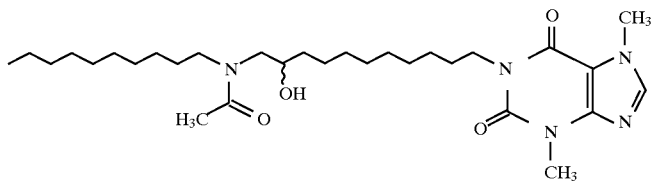

6520 1-[11-(N-Decyl acetamido)-10-hydroxyundecyl]-3,7-dimethylxanthine

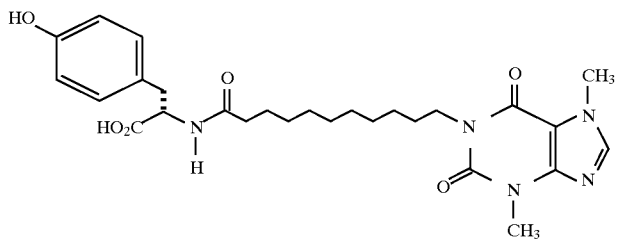

6521 (S)-1-(11-[1-Carboxy-2-(4-hydroxyphenyl)ethylamino]-11-oxoundecyl)-3,7-dimethylxanthine

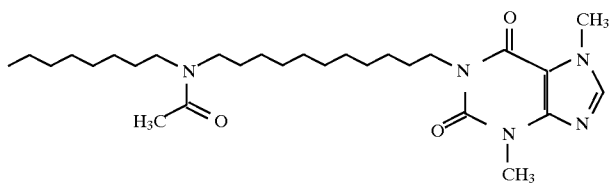

6522 1-[11-(N-Octyl acetamido)undecyl]-3,7-dimethylxanthine

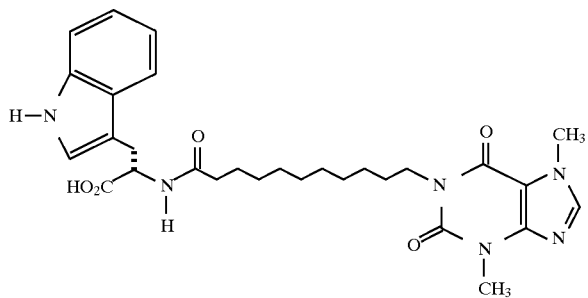

6523 (S)-1-(11-[1-Carboxy-2-(3-Indolyl)ethylamino]-11-oxoundecyl)-3,7-dimethylxanthine

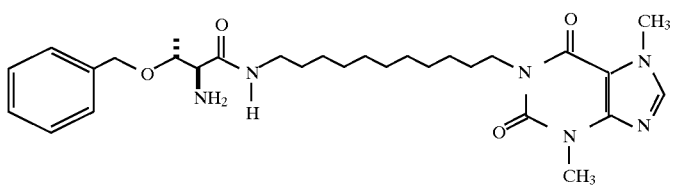

6524 (S)-1-[11-(2-Amino-3-benzyloxybutyronamido)undecyl]-3,7-dimethylxanthine

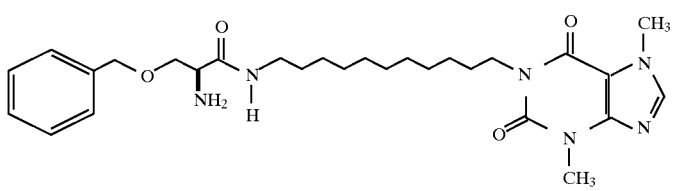

6525 (S)-1-[11-(2-Amino-3-benzyloxypropionamido)undecyl]-3,7-dimethylxanthine

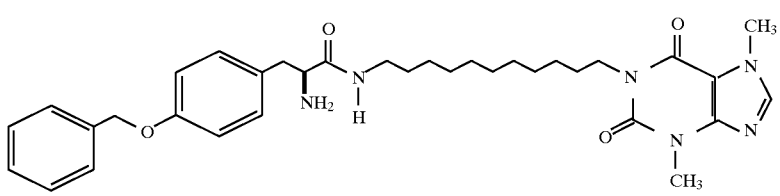

6527 (S)-1-(11-[2-Amino-3-(4-benzyloxyphenyl)propionamido]undecyl)-3,7-dimethylxanthine

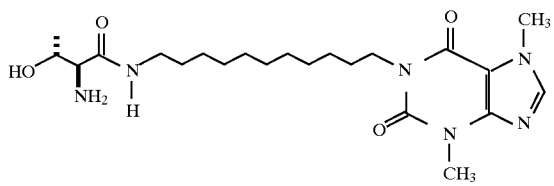

6528 (S)-1-[11-(2-Amino-3-hydroxybutyronamido)undecyl]-3,7-dimethylxanthine

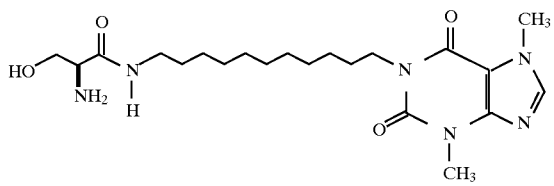

6529 (S)-1-[11-(2-Amino-3-hydroxypropionamido)undecyl]-3,7-dimethylxanthine

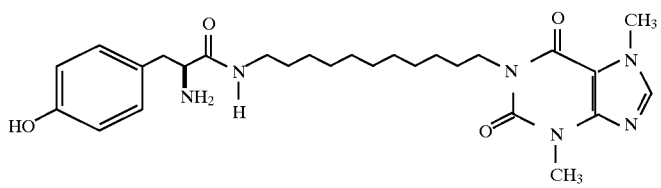

6530 (S)-1-(11-[2-Amino-3-(4-hydroxyphenyl)propionamido]undecyl)-3,7-dimethylxanthine

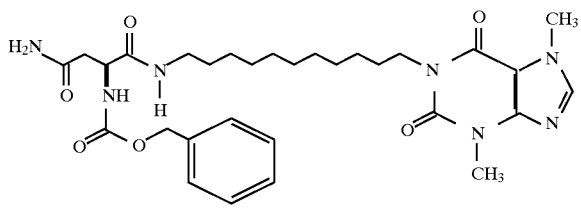

6535 1-(11-[4-Amino-2-carbobenzyloxyamino-4-oxobutyronamido]undecyl)-3,7-dimethylxanthine

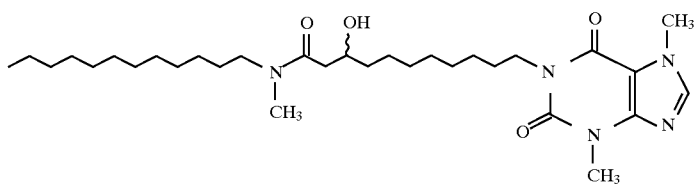

6538 1-(11-Dodecylmethylamino-9-hydroxy-11-oxoundecyl)-3,7-dimethylxanthine

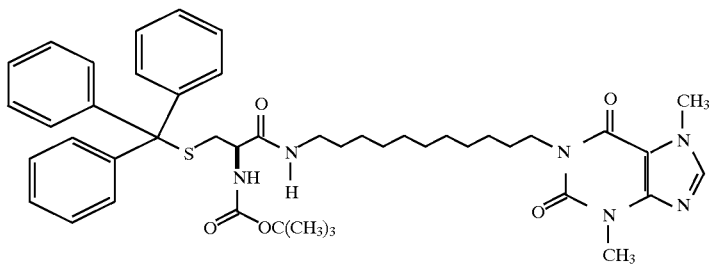

6539 (S)-1-[11-(2-Carbobutoxyamino-3-tritylthiopropionamido)undecyl]-3,7-dimethylxanthine

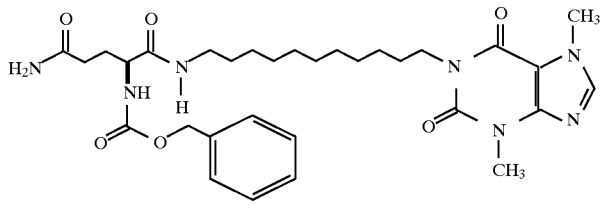

6540  1-(11-[5-Amino-2-carbobenzyloxyamino-5-oxopentanamido]undecyl)-3,7-dimethylxanthine

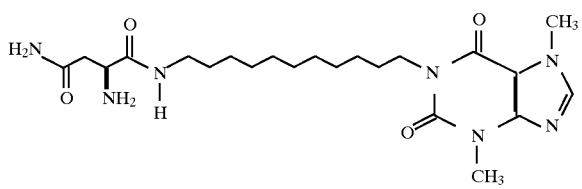

6541  1-(11-[2,4-Diamino-4-oxobutyronamido]undecyl)-3,7-dimethylxanthine

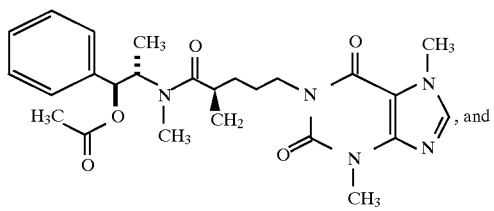

6545  (1'S,2'S,4R)-1-(5-[N-(2-Acetoxy-1-methyl-2-phenylethyl)-N-methylamino]-4-methyl-5-oxopentyl)-3,7-dimethylxanthine Method of Making the Inventive Compounds The invention also provides a process for preparing the inventive compounds. The inventive process utilizes starting materials available to skilled artisans, whether commercially supplied or prepared from other materials commercially available. In addition, some, selected starting materials and intermediates available for use in the inventive process and a corresponding method of synthesis for these selected starting materials are disclosed in U.S. patent applications, Ser. Nos. 08/152,650 and 08/164,081 filed Nov. 12, 1993 and Dec. 8, 1993, respectively, the disclosures of which are incorporated in their entirety herein by reference.

The inventive carboxylic acid-, ester- and amide-substituted compounds of the invention may be prepared by the following general process. Specific, non-limiting examples of synthetic protocols for preparing exemplary compounds of the invention are set forth in the examples which follow.

In a method according to the invention, a compound containing a desired core (intended as a "core moiety" in the inventive compound) undergoes a reaction to produce an anion. Then, the resulting anion may be subsequently reacted with a suitable, substituted ester having at least one other functional group to displace a targeted functional group on the ester, thereby obtaining a compound according to the invention.

In a preliminary reaction, a predetermined amount of a core-containing compound is reacted with a base, a solvent and the suitable substituted ester to obtain an ester product. Again, the substituted ester has at least one functional group which may be substituted in a displacement reaction by the desired core-containing compound.

Preferred bases include, but are not limited to, sodium hydride, sodium amide, sodium alkoxide, lithium hydride, potassium hydride, lithium amide, sodium amide and potassium amide. An especially preferred base is sodium hydride. Preferred solvents may be dimethylsulfoxide, dimethylformamide, or an alcohol. An alcohol may be chosen from among methanol, ethanol or isopropanol. Any substituted ester comprising a chain structure of the inventive compounds may be used in this preliminary reaction, as long as a functional group is present for displacement. Preferred esters may be substituted esters and may be, but are not limited to, halo-substituted esters.

These ester products, which have a composite structure of a core-moiety and ester-containing side chain may then subsequently be converted to an inventive compound having a carboxylic acid-substituted side chain.

In this process, the ester product is reacted with an ester-hydrolyzing agent to obtain an inventive compound having a carboxylic acid-substituted side chain. Representative ester-hydrolyzing agents useful in preparing inventive carboxylic acid-containing inventive compounds may be potassium hydroxide or sodium hydroxide in water, although other ester-hydrolyzing agents are within the scope of the inventive process.

In a halogenation reaction, the carboxylic acid-containing compound above may be reacted with a halogenating agent toacitain an intermediate having a carboxylic acid halide functional group. Although other agents are within the scope of the inventive method, halogenating agents may be chosen from among thionyl chloride, phosphorus trichloride, phosphorus pentachloride, phosphorus oxychloride, thionyl bromide and the like.

Once the intermediate prepared in the step above, containing a carboxylic acid halide functional group is isolated, it is then be reacted with an amine to obtain a corresponding amide-containing inventive compound. In this reaction, the amine compound will contribute to a portion of the final structural configuration of the inventive amide-containing compounds.

Alternatively, a compound containing a desired core may be reacted with a base and substituted-olefin, producing an intermediate olefinic product. The substituted olefin starting material will have a target functional group which will be displaced by an anion of the core-containing compound. In this reaction, a predetermined amount of a core-containing compound is reacted with a suitable base, a solvent and a substituted olefin. Again, the substituted olefin has at least one functional group for displacement.

Preferred bases include, but are not limited to, sodium hydride, sodium amide, sodium alkoxide, lithium hydride, potassium hydride, lithium amide, sodium amide, potassium amide and sodium hydride. Preferred solvents may be dimethylsulfoxide, dimethylformamide, or an alcohol such as, for example, methanol, ethanol or isopropanol. Any substituted olefin comprising a chain structure of the inventive compounds may be used in the preliminary reaction according to the invention. Preferred olefins may be substituted olefins. Preferred substituted olefins include, but are not limited to halo-substituted olefins.

By reacting the intermediate olefinic product previously obtained with an oxidizing agent, a diol is prepared from the olefinic product. Preferred oxidizing agents include, but are not limited to, osmium tetroxide. Preferred oxidizing agents, such as osmium tetroxide may require a catalytic amount of the oxidizing agent in the presence of a regenerating agent. Representative regenerating agents may be 4-methylmorpholine-N-oxide and trimethylamine-N-oxide. An especially preferred regenerating agent is 4-methylmorpholine-N-oxide. In a subsequent halogenation reaction, the resulting diol is converted to an inventive compound using a halogenating agent in the presence of an organic acid. Exemplary halogenating agents include, but are not limited to, hydrogen bromide and hydrogen chloride. Preferred organic acids may be acetic acid and propionic acid.

Also, inventive amide- and ester-substituted compounds according to the invention may also be prepared by reacting a compound containing at least one of an alcohol or amine functional group with a substituted acyl halide or carboxylic acid anhydride. The compound containing at least one alcohol or amine also has as a structural component a core moiety corresponding to a core moiety of the inventive compounds. Starting materials may be obtained commercially or by synthesis from other materials which are commercially available. Some amino alcohol compounds may also be prepared as disclosed in the above-identified copending U.S. patent applications.

A schematic representation of an inventive process for preparing an amide-substituted inventive compound is illustrated as follows:

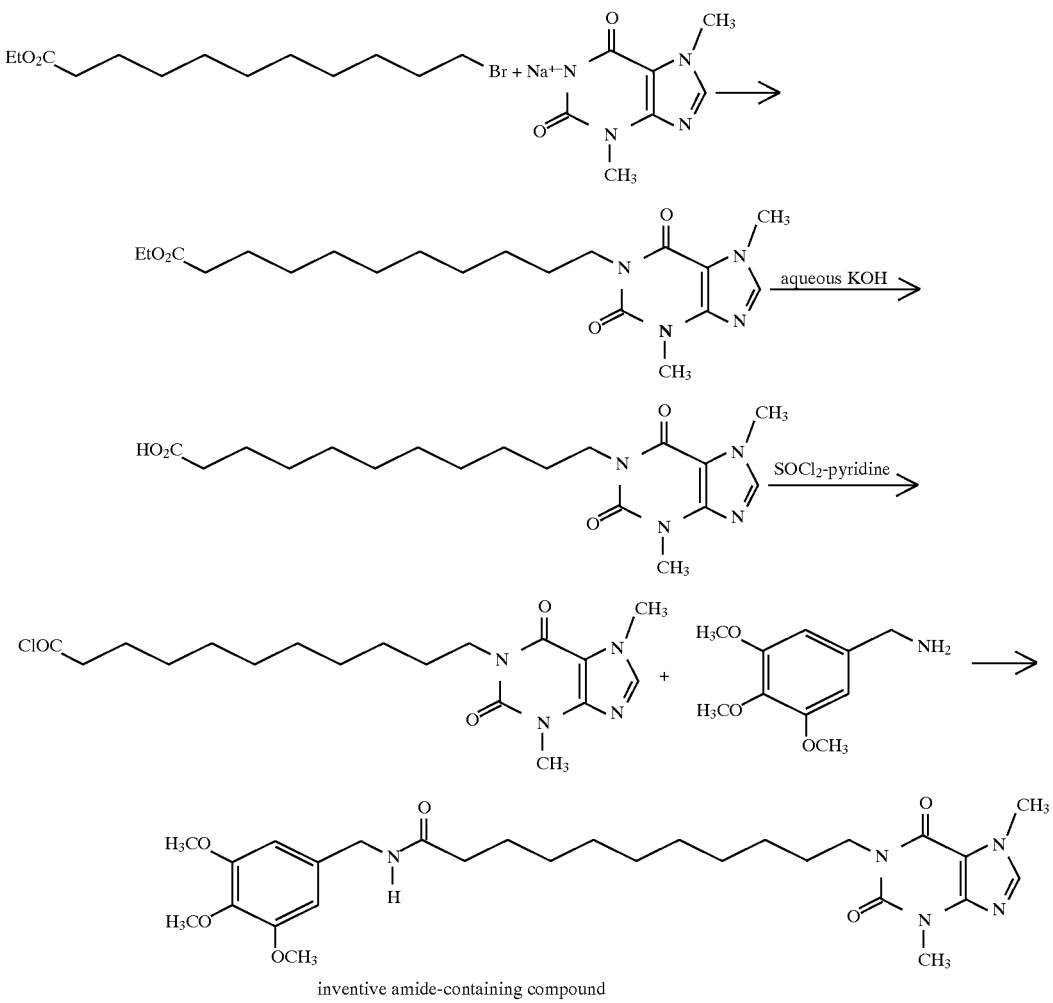

inventive amide-containing compound

Uses of the Invention Compounds and Pharmaceutical Formulations

The inventive compounds provide a method for maintaining homeostasis in cells contacted by primary stimuli by mitigating the effects of these primary stimuli on the secondary signaling pathways invoked within seconds of a primary stimulus. For example, administration of an inventive compound in vivo or ex vivo provides a method to modify cellular behavior, the method comprising contacting cells (in vivo or ex vivo), whose behavior is to be modified, with an effective amount of an inventive compound or a pharmaceutical composition thereof. The method is a method to: (1) inhibit proliferation of tumor cells, being; (2) suppress activation of T-cells by antigen or IL-2 stimulation being; (3) suppress activation of monocytemacrophage cells by endotoxin, TNF, IL-1 or GM-CSF stimulation, being; (4) suppress antibody production of B-cells in response to an antigen, IL-4 or CD40 ligand, being; (5) inhibit the proliferation of smooth muscle cells in response to growth factors capable of stimulating said proliferation, being; (6) lower systemic vascular resistance conferred by endothelial cells, being; (7) lower systemic vascular resistance induced by endothelial cells, being; (8) lower expression of adhesion molecules induced by enhancers thereof, being; (9) suppress the activation of T-cells and macrophages by HIV, being; (10) inhibit the proliferation of kidney mesangial cells in response to stimulation by IL-1 and/or MIP-1α and/or PDGF and/or FGF, being; (11) enhance the resistance of kidney glomerular or tubular cells to cyclosporin A or amphotericin B, being; (12) prevent the release of MIP-1α IL-1, TNF, or endotoxin stimulated monocytes and macrophages; (13) prevent the release of platelet activating factor by IL-1, TNF, or endotoxin treated megakaryocytes, fibroblastic cells, and macrophages; (14) prevent the downregulation of receptors for cytokines in TNF-treated hematopoietic progenitor cells, being; (15) suppress the production of metalloproteases in IL-1-stimulated or TNF-stimulated glomerular epithelial cells or synovial cells, being; (16) enhance the resistance of gastrointestinal or pulmonary epithelial cells to cytotoxic drugs or radiation, being; (17) enhance the antitumor effect of a non-allylating antitumor agent, being; (18) to inhibit the production of osteoclast activating factor in response to IL-1, being; (19) inhibit degranulation in response to IgE, being; (20) enhance the release of adrenergic neural transmitters, dopamine, norepinephrine, or epinephrine, or the neurotransmitter, acetylcholine, being; (21) modulate the post-synaptic "slow current" effects of the adrenergic neurotransmitters dopamine, epinephrine, or norepinephrine, or the neurotransmitter acetylcholine, being; (22) suppress signaling by neurotransmitters including acetyl choline, leuenkephalin and serotonin; or (23) increase seizure threshold.

Indications useful for administering compounds of the invention include, but are not limited to: the presence of a tumor burden, a hormone-related disorder, a neurological disorder, an autoimmune disease, inflammation, restenosis, coronary artery disease, atherosclerosis, hypertension, unwanted immune response (such as allograft reactions), viral infection, nephritis, mucositis, and various allergic responses. Allergic responses include, but are not limited to, acute allergic response and thus rhinorrhea, sinus drainage, diffuse tissue edema, and generalized pruritus. As well as the following, other chronic allergic responses include, but are not limited to, dizziness, diarrhea, tissue hyperemia, and lacrimal swelling with localized lymphocyte infiltration. Allergic reactions are also associated with leukotriene release and the distal effects thereof, including asthmatic symptoms (e.g., development of airway obstruction, a decrease in FEV1, changes in vital capacity, and extensive mucus production).

Other suitable subjects for the administration of compounds of the invention, include patients: being administered other cytotoxic agents for the treatment of tumors, such as chemotherapeutic agents or irradiation therapy; suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; exhibiting unwanted smooth muscle cell proliferation in the form of, for example, restenosis, such as patients undergoing cardiac surgery; afflicted with autoimmune diseases, thus requiring deactivation of T and B cells, and having neurological disorders.

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiring such treatment as an effective oral, parenteral, or intravenous sublethal dose of about 50 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Pharmaceutical Formulations

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider. Parenteral includes, but is not limited to, intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier, optionally containing a parenterally acceptable oil, for example polyethylene glycol, polyvinylpyrrolidone, lecithin, arachis oil, or sesame oil. The daily dosage for treatment of sepsis or another severe inflammatory condition via parenteral administration is suitable from about 0.001 mg/kg to about 40 mg/kg, preferably from about 0.01 mg/kg to about 20 mg/kg of an inventive compound or a pharmaceutically acceptable salt thereof calculated as the free base.

The inventive compounds may be administered orally. The daily dosage regimen for oral administration is suitably from about 0.1 mg/kg to about 1000 mg/kg per day. For administration the dosage is suitably from about 0.001 mg/kg to about 40 mg/kg of the inventive compound or a pharmaceutically acceptable salt thereof, calculated as the free base. The active ingredient may be administered from 1 to 6 times a day, sufficient to exhibit activity.

The inventive compounds may be administered by inhalation (e.g., intranasal or oral). Appropriate dosage forms include, but are not limited to, an aerosol or a metered dose inhaler, as prepared by conventional techniques. The daily dosage is suitably from about 0.001 mg/kg to about 40 mg/kg of the inventive compound or a pharmaceutically acceptable salt thereof, calculated as the free base. Typical compounds for inhalation are in the form of a solution, suspension or emulsion that may be administered as a dry powder or in the form of an aerosol using a conventional propellant.

The invention is illustrated by the following examples which should not be regarded as limiting the invention in any way.

EXAMPLE 1

This example is a synthesis for inventive compound no. 1527 (see above for chemical name and structure). A mixture of theobromine (1.0 g, 5.5 mmol, available from Sigma) and a solution (20 ml) of 50% sodium hydride in oil (264 mg, 5.5 mmol) in dimethylsulfoxide was stirred for 50 minutes, followed by addition of 6-bromo-1-hexanol (1.0 g, 5.5 mmol, available from Aldrich). After stirring for 18 hours, the solution was treated with 50 ml of water and then extracted with two 25 ml aliquots of hexanes. The aqueous phase was extracted with three 35 ml aliquots of 25% ethanol-dichloromethane. The combined ethanol-dichloromethane extracts were dried over magnesium sulfate and then the solvents were evaporated under vacuum. The remaining dimethylsulfoxide was removed by distillation under full pump vacuum, producing 1.4 g of a white powder, 1-(6-hydroxyhexyl)-3,7-dimethylxanthine (5.0 mmol, 91% yield).

A solution (5 ml) of chloroacetyl chloride (339 mg; 3 mmol) in dichloromethane was added dropwise at 0° C. to a solution (5 ml) of 1-(6-hydroxyhexyl)-3,7-dimethylxanthine (560 mg; 2 mmol) and triethylamine (607.2 mg; 6 mmol) in dichloromethane. The reaction was slowly warmed to room temperature and stirred overnight. The reaction was quenched with saturated sodium bicarbonate solution (5 ml) and extracted with three 50 ml aliquots of dichloromethane. The combined organic extracts were washed with 1% dilute hydrogen chloride (15 ml), followed by water (15 ml) and finally with brine solution (15 ml), dried over anhydrous magnesium sulfate and concentrated under reduced pressure. A crude product obtained was further purified by flash chromatography over silica gel using a 20% hexane/ethyl acetate eluant, resulting in 296 mg of compound no. 1527 (50.1% yield).

EXAMPLE 2

Theobromine (11.9 g, 66 mmol, available from Sigma) was added to a mixture of bromohexene (10.7 g, 66 mmol, available from Aldrich) and sodium hydride (1.58 g, 66 mmol) in dimethylsulfoxide (100 ml) and the resulting mixture stirred for 43 hours. The solution was treated with water (200 ml) and then extracted with three 80 ml aliquots of dichloromethane. The combined extracts were washed with three 100 ml aliquots of water and dried over magnesium sulfate. The solvent was evaporated under vacuum, leaving 17 g of a white powder, 1-(5-hexenyl)-3,7-dimethylxanthine (65 mmol, 98% yield).

Six drops of 2.5% osmium tetraoxide in t-butanol were added to a mixture of 1-(5-hexenyl)-3,7-dimethylxanthine (1.07 g, 4.1 mmol), as prepared above and N-methylmorpholine-N-oxide (1.44 g, 12.3 mmol) in water (20 ml) and acetone (10 ml). After stirring the resulting mixture for 48 hours, the mixture was treated with 20% aqueous sodium dithionite solution (20 ml). After 2 minutes, the mixture was extracted with three 30 ml aliquots of a 25% ethanol-dichloromethane solution. The combined extracts were dried over magnesium sulfate and the solvent was evaporated under vacuum, leaving 750 mg of a white powder, 1-(5,6-dihydroxyhexyl)-3,7-dimethylxanthine (2.53 mmol, 62% yield).

A solution of 1-(5,6-dihydroxyhexyl)-3,7-dimethylxanthine (0.50 g, 1.7 mmol) and 1,1'-carbonyldiimidazole (1.10 g, 6.8 mmol) was refluxed for 20 hours. Water (30 ml) was added and the mixture was extracted with three 50 ml aliquots of dichloromethane. The combined organic layers were washed with two 30 ml aliquots of water and dried over sodium sulfate. The solvent was removed under vacuum. A residue was further purified by chromatography over silica using an ethyl acetate-10% ethanol eluant, yielding 180 mg of compound no. 1578 (33% yield).

EXAMPLE 3

Methanesulfonyl chloride (2.20 g, 1.5 ml, 19.2 mmol) was added to a solution (100 ml) of 9-decene-1-ol (3.00 g, 19.2 mmol, available from Aldrich) in dichloromethane at 0° C., followed by addition of triethylamine (2.91 g, 28.8 mmol). After stirring was continued for 15 minutes at 0° C., the reaction was allowed to warm to room temperature. After 2 hours, the reaction mixture was poured into water (100 ml) and extracted with three 60 ml aliquots of dichloromethane. The combined organic portions were dried over sodium sulfate and the solvent was evaporated under vacuum, leaving a yellow oil mesylate (4.52 g, 100%), which was used without further purification.

Theobromine (3.45 g, 19.2 mmol) was added to a suspension (30 ml) of sodium hydride (461 mg, 19.2 mmol) in dimethylsulfoxide. After 15 minutes, the 9-decenylmesylate (2.25 g, 11 mmol) was added and the reaction stirred for 18 hours at 25° C., then for 40 minutes at 100° C. The mixture was then poured into water (100 ml) and extracted with three 50 ml aliquots of dichloromethane. The combined organic portions were washed with saturated salt solution (60 ml) and dried over magnesium sulfate. Evaporating the solvent under vacuum left a white solid residue. Recrystallization of the residue in ether produced 3.40 g of 1-(9-decenyl)-3,7-dimethylxanthine (56% yield).

1-(9-Decenyl)-3,7-dimethylxanthine (3.2 g, 10.1 mmol), 4-methylmorpholine-N-oxide (1.41 g, 12 mmol), 3 drops of 2.5% osmium tetroxide solution in t-butanol, acetone (40 ml) and water (10 ml) were stirred for 24 hours. Following addition of 5 ml of a saturated solution of sodium dithionite and a further 15 minutes of stirring, the reaction mixture was extracted with four 50 ml aliquots of 25% ethanol/dichloromethane. The combined organic portions were dried over sodium sulfate. Evaporating the solvents left a white solid residue, which upon recrystallization in ethanol produced 3.3 g of 1-(9,10-dihydroxydecyl)-3,7-dimethylxanthine (93% yield).

1-(9,10-Dihydroxydecyl)-3,7-dimethylxanthine (2.11 g, 6 mmol), prepared above, was stirred with hydrogen bromide (3.58 ml, 4.85 g of a 30% solution in acetic acid, 18 mmol) for 90 minutes. The mixture was then added to a flask containing 40 ml aqueous sodium bicarbonate solution (5 g) and 50 ml dichloromethane. After 10 minutes of vigorous stirring the layers were separated and the aqueous portion washed with two 50 ml aliquots of dichloromethane. The organic portions were combined, dried over sodium sulfate, and evaporating the solvent produced 2.72 g of a yellow oil, inventive compound no. 1583 (100% yield).

EXAMPLE 4

Sodium hydride (343 mg, 14 mmol) was added to a stirring solution of 1-methylthymine (2.00 g, 14 mmol) in dimethylsulfoxide (40 ml). After 15 minutes, 9-bromo-1-nonene (2.93 g, 14 mmol, available from Alfebro) was added and the resulting mixture stirred for 20 hours. The reaction was poured into water (40 ml) and extracted with three 50 ml aliquots of dichloromethane. The organic layers were combined, washed with water (40 ml) and saturated aqueous salt solution (20 ml). After drying the washed organic layers over sodium sulfate, the solvent was evaporated, leaving a colorless oil, 3-(8-nonenyl)-1-methylthymine, which solidified upon standing (2.76 g, 73% yield).

A solution of 3-(8-nonenyl)-1-methylthymine (2.63 g, 9.9 mmol), prepared above, 4-methylmorpholine-N oxide (1.39 g, 12 mmol), and potassium osmate (IV) dihydrate (7 mg, $2 \times 10^{-5}$ mol) in acetone (20 ml) anhours. After addition of a satura for 18 hours. After addition of a saturated aqueous solution of sodium hydrosulfite (10 ml) and 15 minutes of stirring, the reaction mixture was extracted with dichloromethane (50 ml) and with two 50 ml aliquots of dichloromethane/20% methanol. The combined organic layers were washed with water (15 ml) and saturated aqueous salt solution (15 ml), and then dried over sodium sulfate. The solvent was evaporated under vacuum, leaving a white solid residue. Recrystallization of the solid in ethanol yielded 2.68 g of 3-(8,9-dihydroxynonyl)-1-methylthymine (91% yield).

A mixture of 3-(8,9-dihydroxynonyl)-1-methylthymine (2.16 g, 7.6 mmol), prepared above, and a 30% solution of hydrogen bromide in acetic acid (4.5 ml, 23 mmol) was stirred for 1 hour. The reaction mixture was added slowly to a beaker containing sodium bicarbonate (8.4 g, 0.1 mol), ice water (30 ml), and dichloromethane (30 ml). The layers were separated, and the aqueous layer extracted with two 60 ml aliquots of dichloromethane. The combined organic layers were washed with water (30 ml) and saturated aqueous salt solution (30 ml). The washed organic layers were then dried over sodium sulfate. Evaporation of the solvent produced 2.59 g of a slightly orange oil, inventive compound no. 1908 (85% yield).

EXAMPLE 5

This example is a method of synthesis for inventive compound no. 2573 (see above for chemical name and compound). A mixture of theobromine (17.64 g, 98 mmol) and sodium hydride (2.35 g, 98 mmol) in dimethylsulfoxide (250 ml) was stirred for 15 minutes. After addition of 9-bromo-1-nonene (20.0 g, 98 mmol, available from Alfebro) stirring was continued at ambient temperature for 3 days. The reaction mixture was then poured into water (300 ml) and extracted with four 200 ml aliquots of dichloromethane. The combined organic layers were washed with two 150 ml aliquots of saturated aqueous salt solution and the washed layers dried over sodium sulfate. Evaporating the solvent under vacuum resulted in a thick oil, which resulted in 24.34 g of white crystals after cooling a solution of the thick oil in a minimum of dichloromethane and ether 1-(8-nonenyl)-3,7-dimethylxanthine (77.5 mmol, 99% yield).

A solution of 1-(8-nonenyl)-3,7-dimethylxanthine (810 mg, 2.7 mmol), prepared above, 4-methylmorpholine-N-oxide (340 mg, 2.9 mmol) and 3 drops of 2.5% osmium tetroxide in t-butanol, acetone (20 ml) and water (20 ml) was stirred for 24 hours, followed by addition of saturated aqueous sodium dithionite solution (5 ml). After stirring the resulting mixture for 15 minutes, the reaction mixture was extracted with four 50 ml aliquots of 25% ethanol-dichloromethane. The combined organic layers were dried over sodium sulfate, and the solvent evaporated under vacuum. A resulting solid residue was recrystallized in ethanol-chloroform, producing 490 mg of 1-(8,9-dihydroxynonyl)-3,7-dimethylxanthine (54% yield).

A mixture of 1-(8,9-dihydroxynonyl)-3,7-dimethylxanthine, prepared above, and 30% hydrogen bromide in acetic acid (0.8 ml, 3.90 mmol) was stirred for 90 minutes. The solution was poured into a mixture of water (10 ml), sodium bicarbonate (1.35 g, and dichloromethane (10 ml). After 10 minutes of vigorous stirring, the layers were separated and the aqueous portion was extracted with three 15 ml aliquots of dichloromethane. The combined organic phases were dried over sodium sulfate and the solvent was evaporated under vacuum, leaving 550 mg of a yellow oil, 1-(8-acetoxy-9-bromononyl)-3,7-dimethylxanthine (96% yield). Without further purification, the oil was dissolved in methanol (5 ml), to which a 1 M solution of sodium methoxide in methanol (4.1 ml, 4.1 mmol) was added. After 30 minutes, the reaction mixture was poured into water (30 ml) was extracted with three 40 ml aliquots of dichloromethane. The combined organic layers were dried over sodium sulfate. Evaporating the solvents under vacuum left a solid residue. Recrystallization in dichloromethane-petroleum ether yielded 380 mg of 1-(8,9-oxidononyl)-3,7-dimethylxanthine (91% yield).

A mixture of 1-(8,9-oxidononyl)-3,7-dimethylxanthine (0.50 g, 1.6 mmol), prepared above and lithium perchlorate (166 mg, 1.6 mmol) was stirred in anhydrous acetonitrile (40 ml). After addition of dodecylamine (1.48 g, 8.0 mmol, available from Aldrich), the mixture was stirred at reflux for 4 hours. After cooling, dichloromethane (50 ml) was added and the mixture was washed with water (30 ml) and saturated aqueous salt solution (30 ml), and then dried over sodium sulfate. The solvent was removed under vacuum, leaving a white residue. Further purification by chromatography over silica using a dichloromethane/5% methanol eluant, produced 263 mg of a white solid, inventive compound no. 2573 (33% yield).

EXAMPLE 6

This example is a method of synthesis for inventive compound no. 3508. Triphenylphosphine (5.24 g, 20 mmol) was added incrementally to a solution of oleyl alcohol (5.37 g, 20 mmol) and carbontetrabromide (6.63 g, 20 mmol) in 400 ml of dichloromethane, the resulting reaction mixture being stirred for an hour at room temperature. Removing the solvent under reduced pressure, left a residue, which was extracted with three 200 ml aliquots of hexane. Further purification by flash chromatography over silica gel using a hexane eluant produced 5.82 g of 1-bromo-9-octadecene (88% yield).

Sodium hydride (95%, 84 mg, 3.5 mmol) was added to a solution of theobromine (0.595 g, 3.2 mmol) in dimethylsulfoxide (15 ml). After 20 minutes of stirring, 1-bromo-9-octadecene (0.995 g, 3 mmol), prepared above, was added. After 6 hours of stirring at room temperature, the reaction mixture was warmed to 60° C. over 3 hours and then poured into a separatory funnel containing 50 ml of water. The reaction mixture was extracted with five 40 ml aliquots of dichloromethane. The organic extracts were combined, washed with water (50 ml) and brine (50 ml) and dried over anhydrous magnesium sulfate. Removing the solvent under reduced pressure resulted in a crude product further purified by flash chromatography over silica gel using a 30% acetone/petroleum ether eluant, yielding 0.44 g of 1-(9-octadecenyl)-3,7-dimethylxanthine (34 % yield).

A solution of 1-(9-octadecenyl)-3,7-dimethylxanthine (0.15 g, 0.35 mmol), 4-methylmorpholine-N-oxide (49 mg, 0.42 mmol, 1.2 equivalents.) and potassium osmate dihydrate (1 mg) in acetone (4 ml) and water (1 ml) was stirred for 6 hours. A solution of 20% aqueous sodium sulphite (2 ml) was added and stirred for 30 minutes. The reaction mixture was extracted with four 10 ml aliquots of 25% ethanol/dichloromethane. The combined organic extracts were dried over anhydrous magnesium sulfate, the solvent evaporated under reduced pressure and a residue purified by flash chromatography over silica gel using a methanol(5%)/dichloromethane eluant, yielding 0.65 g of 1-(9,10-dihydroxyoctadecyl)-3,7-dimethylxanthine (40.4% yield).

A 50 ml RB flask fitted with a dropping funnel, magnetic stirring bar and an argon inlet was placed in a solution of 1-(9,10-dihydroxyoctadecyl)-3,7-dimethylxanthine (464 mg; 1 mmol) and triphosgene (148.37 mg; 0.5 mmol) in anhydrous dichloromethane. The resulting mixture was cooled to 0° C. A solution of pyridine (58.2 mg; 2 mmol) in anhydrous dichloromethane (3 ml) was added dropwise and the reaction mixture was warmed to room temperature and stirred for 6 hours. The reaction mixture was then diluted with water (20 ml) and extracted with three 50 ml aliquots of dichloromethane. The combined organic extract was washed with water (50 ml), saturated copper sulphate solution (50 ml), water (50 ml), and brine solution (50 ml) and dried over anhydrous magnesium sulfate. Evaporating the solvent under reduced pressure left a residue which was further purified by flash chromatography over silica gel using a 50% ethyl acetate/hexane eluant, resulting in 200 mg of compound no. 3508 (40.8% yield).

EXAMPLE 7

This example is a method of synthesis for inventive compound no. 3537. Sodium hydride (95%, 1.26 g, 50 mmol) was added to a solution of theobromine (7.2 g, 40 mmol) in dimethylsulfoxide (300 ml). After 20 minutes of stirring, undecenylmesylate (7.95 g, 30 mmol) was added and the resulting mixture stirred for 12 hours at room temperature. The reaction was warmed to 70°–80° C.' and stirred for 4 hours. The reaction mixture was then poured into a separatory funnel containing water (1 L) and extracted with five 200 ml aliquots of dichloromethane. The organic extracts were combined, washed with water (100 ml) and brine (100 ml) and dried over anhydrous magnesium sulfate. The solvent was evaporated under reduced pressure, resulting in a crude product, which was further purified by flash chromatography over silica gel using a 20% hexane/dichloromethane eluant producing 4.6 g of 1-(10-undecenyi)-3,7-dimethylxanthine (46.3% yield).

A solution of 1-(10-undecenyl)-3,7-dimethylxanthine (4.3 g, 13 mmol), prepared above, 4-methylmorpholine-N-oxide (1.942 g, 16.6 mmol) and potassium osmate dihydrate (9.5 mg, 0.026 mmol) in acetone (45 ml) and water (10 ml) was stirred for 6 hours. A solution of 20% aqueous sodium sulphite (12 ml) was added and stirred for 30 minutes. The reaction mixture was extracted with four 100 ml aliquots of 25% ethanol/dichloromethane. The combined organic extracts were dried over anhydrous magnesium sulfate. Evaporating the solvent under reduced pressure left a residue, which upon subsequent purification by flash chromatography over silica gel using a methanol (5%)/dichloromethane eluant produced 3.6 g of 1-(10, 11-dihydroxyundecanyl)-3,7-dimethylxanthine (76% yield).

1-(10, 11-Dihydroxyundecanyl)-3,7-dimethylxanthine (3.6 g, 10 mmol) was stirred with hydrogen bromide (6.2 ml, 8.4 g of a 30% solution in acetic acid, 31.1 mmol) for 90 minutes. The mixture was then added to a flask containing 100 ml aqueous sodium bicarbonate solution and 75 ml dichloromethane. After 10 minutes of vigorous stirring, the layers were separated and the aqueous portion washed with three 75 ml aliquots of dichloromethane. The organic portions were combined and dried over magnesium sulfate. Evaporating the solvent left 3.6 g of 1-(10-acetoxy-11-bromoundecanyl)-3,7-dimethylxanthine. Without further purification, 1 -(10-acetoxy- 11 -bromoundecanyl)-3,7-dimethylxanthine was taken up in 25 ml of methanol and treated with a solution of sodium methoxide (prepared from 0.28 g, 12.2 mmol sodium, and 25 ml methanol). After 30 minutes, most of the solvent was removed under reduced pressure and the residue was extracted with three 75 ml aliquots of dichloromethane. The organic portions were combined and dried over magnesium sulfate. The solvent was evaporated under reduced pressure, leaving an off-white solid. Further purification of the off-white solid by column chromatography over silica gel using a dichloromethane/(3%) methanol eluant provided 2.0 g of 1-(10,11-oxidoundecanyl)-3,7-dimethylxanthine (57.5% yield).

Octylamine (3.4 ml, 21 mmol) was added to a stirring mixture of 1-(10,11-oxidoundecyl)-3,7-dimethylxanthine (5.00 g, 14.4 mmol), prepared above, and lithium perchlorate (1.69 g, 16 mmol) in anhydrous acetonitrile (60 ml). Stirring was continued for 16 hours at 50° C. After cooling to ambient temperature, water (100 ml) was added, and the mixture was extracted with three 100 ml aliquots of dichloromethane-10% methanol. The combined organic extracts were washed with aqueous saturated salt solution (150 ml) and dried over sodium sulfate. The solvent was removed under vacuum, leaving a solid, which was recrystallized twice in dichloromethane/ether/hexane, producing 5.76 g of a white powder, 1-(11-octylamino-10-hydroxyundecyl)-3,7-dimethylxanthine (84% yield).

A solution of 1-(11-octylamino-10-hydroxyundecyl)-3,7-dimethylxanthine (1.70 g, 3.0 mmol), prepared above, in acetic anhydride (5 ml) was heated for 2 hours at 90° C. After cooling, methanol (10 ml) was added and the mixture was stirred for 30 minutes. After addition of water (20 ml), the mixture was extracted with three 40 ml aliquots of dichloromethane. The combined organic layers were washed with water (15 ml) and saturated aqueous salt solution (15 ml). After the solution was dried over sodium sulfate, the solvent was evaporated, leaving a yellow oil residue. The residue was further purified by chromatography over neutral activity II alumina using a dichloromethane-5% methanol eluant, resulting in 1.43 g of a colorless oil, inventive compound no. 3537 (2% yield), which solidified upon standing.

EXAMPLE 8

This example is a method of synthesis for inventive compound no. 3541 (see above for chemical name and structure). Sodium hydride (312 mg, 13 mmol) was added to a solution of octanol (10 ml) in toluene (20 ml). After bubbling ceased, 1-(10,11-oxidoundecanyl)-3,7-dimethylxanthine (2.50 g, 7.2 mmol), prepared in example 7 above, was added to the mixture, which was subsequently stirred for 3 hours at 60–70° C. After cooling, the mixture was added to a solution of saturated aqueous solution of ammonium chloride (15 ml) and water (10 ml) and extracted with three 50 ml aliquots of dichloromethane. The combined organic layers were washed with saturated aqueous salt solution and dried over sodium sulfate. Evaporation of the solvents under vacuum left a solid residue, which when purified by chromatography over neutral activity II alumina using a dichloromethane eluant produced recovered epoxide (411 mg) and 1.34 g of 1-(11-octyloxy-10-hydroxyundecyl)-3,7-dimethylxanthine (49% yield).

A mixture of 1-(11-octyloxy-10-hydroxyundecyl)-3,7-dimethylxanthine (0.31 g, 0.6 mmol), prepared above, and acetic anhydride (4 ml) was heated at 90° C. for 2 hours. After cooling to ambient temperature, dichloromethane (40 ml) and saturated sodium bicarbonate solution (50 ml) were added. The organic layer was separated, and the aqueous layer was extracted with dichloromethane (50 ml). The combined organic layers were washed with water (10 ml) and saturated aqueous salt solution (10 ml). After the solution was dried over sodium sulfate, the solvent was removed, leaving an oily residue. The residue was purified by chromatography over silica using a dichloromethane-10% methanol eluant, producing 149 mg of inventive compound no. 3541 (49% yield).

EXAMPLE 9

This example is a method of synthesis for inventive compound no. 3549 (see above for chemical name and structure). A solution of 11-bromoundecanoic acid (5.70 g, 22 mmol, available from Aldrich) and p-toluenesulfonic acid (0.1 g) in absolute ethanol (100 ml) was refluxed for 3 hours. A saturated aqueous sodium bicarbonate solution (40 ml) was added and the reaction mixture then extracted with three 70 ml aliquots of dichloromethane. The combined extracts were washed with water (50 ml) and saturated aqueous salt solution (50 ml) and the solvent was evaporated, leaving a colorless oil. Ethyl 11-bromoundecanoate (5.92 g, 94% yield) was collected during distillation (2 mm) at 135° C. A solution of this bromoester (5.92 g, 20 mmol) and 1-sodiotheobromine (4.08 g, 20 mmol) in dimethylsulfoxide (80 ml) was stirred for 18 hours at ambient temperature. The mixture was added to water (100 ml) and dichloromethane (100 ml). The aqueous layer was extracted with two 80 ml aliquots of dichloromethane. The combined organic layers were washed with water (80 ml) and saturated aqueous salt solution (80 ml), dried over magnesium sulfate, and the solvent was evaporated under vacuum, leaving a white solid residue. The residue was recrystallized in dichloromethane/ether/hexane, yielding 4.95 g of 1-(ethyl 11-yl-undecanoate)-3,7-dimethylxanthine (62% yield).

A solution of potassium hydroxide (0.50 g, 9.0 mmol) in water (1 ml) was added to a stirring suspension of 1-(ethyl 11-yl-undecanoate)-3,7-dimethylxanthine (2.52 g, 6.4 mmol), prepared above, in methanol (15 ml). The mixture was warmed until homogeneous, and the stirring was continued overnight at ambient temperature. Water (10 ml) was added to the reaction mixture, followed by a 5% solution of sulfuric acid (10 ml). The precipitate was filtered off and washed with ether, then dried under vacuum, resulting in 2.12 g of inventive compound no. 3549 (91% yield).

EXAMPLE 10

This example is a method of synthesis for inventive compound no. 3554 (see above for chemical name and structure). A solution of 1-(11-yl-undecanoic acid)-3,7-dimethylxanthine (1.62 g, 4.5 mmol), prepared in example 10 above, and thionyl chloride (0.5 ml, 6.7 mmol) in toluene (5 ml) was heated at 80° C. for 1 hour and then cooled. The solvent was evaporated under a nitrogen stream. The resulting acid chloride was taken up in dichloromethane (20 ml), and 1-octylamine (2 ml, 11 mmol) was added by syringe to the stirring solution. After 2 hours, water (50 ml) was added and the mixture was extracted with three 50 ml aliquots of dichloromethane. The combined organic extracts were washed with 5% hydrochloric acid (100 ml) and saturated aqueous salt solution (60 ml) and then dried over sodium sulfate. The solvent was evaporated under vacuum, leaving a residue, which was further purified by chromatography over basic activity II alumina using a dichloromethane/10% methanol eluant, yielding 1.47 g of compound no. 3554 as a white solid (69% yield).

EXAMPLE 11

This example is a method of synthesis for inventive compound no. 3564 (see above for chemical name and structure). Tetradecylamine (797 mg, 3.7 mmol) was added to a stirring mixture of 1-(10,11-oxidoundecanyl)-3,7- dimethylxanthine (1.00 g, 2.9 mmol), prepared in example 7 above, and lithium perchlorate (309 mg, 2.9 mmol) in anhydrous acetonitrile (20 ml). Stirring was continued for 4 hours at 60° C. After cooling to ambient temperature, water (50 ml) was added, and the mixture was extracted with three 100 ml aliquots of dichloromethane. The combined organic extracts were washed with aqueous saturated salt solution and dried over sodium sulfate. The solvent was removed under vacuum, leaving a solid residue, which was purified by chromatography over neutral activity II alumina using a dichloromethane-3% methanol eluant, resulting in 550 mg of a white powder, 1-(11-tetradecylamino-10-hydroxyundecyl)-3,7-dimethylxanthine (34% yield).

A solution of 1-(11-tetradecylamino-10-hydroxyundecyl)-3,7-dimethylxanthine (600 mg, 1.1 mmol) and acetic anhydride (0.6 ml, 6.4 mmol) in pyridine (15 ml) was stirred at ambient temperature for 20 hours. After addition of dichloromethane (100 ml) the mixture was washed with two 50 ml aliquots of 10% aqueous hydrochloric acid and saturated aqueous salt solution (50 ml), and then dried over magnesium sulfate. The solvent was removed under vacuum, leaving a residue, which was then purified by chromatography over neutral activity II alumina using a dichloromethane-3% methanol eluant, resulting in 475 mg of inventive compound no. 3564 (69% yield).

EXAMPLE 12

This example is a method of synthesis for inventive compound no. 3577 (see above for chemical name and structure). Under an argon atmosphere, oxalyl chloride (0.72 ml, 8.3 mmol) was added to a slurry of 1-(11-yl-undecanoic acid)-3,7-dimethylxanthine (2.0 g, 5.5 mmol), prepared in example 9 above, in dichloromethane (20 ml). The reaction was heated to reflux and allowed to stir for 1 hour. The resulting solution was cooled to ambient temperature and then slowly transferred to a stirring solution of 3,4,5-trimethoxybenzylamine (2.8 ml, 16.5 mmol) in dichloromethane (20 ml), followed by cooling to 0° C. After 2 hours of stirring at ambient temperature, the reaction was poured into 3% aqueous hydrogen chloride solution (100 ml), followed by saturated aqueous salt solution (40 ml). The mixture was extracted with three 50 ml aliquots of dichloromethane. The combined organic layers were washed with saturated aqueous salt solution (50 ml) and dried over magnesium sulfate. The solvents were evaporated under reduced pressure, leaving a crude yellow residue. Column chromatography over alumina using an ethyl acetate/ethyl acetate-methanol eluant and subsequent recrystallization from ethyl acetate produced 0.98 g of a white solid, inventive compound no. 3577 (33% yield).

EXAMPLE 13

This example shows an inhibitive effect of inventive compounds nos. 3549 and 3546 on murine thymocyte proliferation stimulated by Concanavalin A (ConA) and interleukin-2 (IL-2). This assay is an in vitro, predictive model of a compound's therapeutic potential in treating or preventing autoimmune, immune or inflammatory diseases. Procedurally, thymuses were obtained from normal, female Balb/C mice. The thymuses were dissociated and plated into 96-well plates at a density of $2 \times 10^5$ cells/well. ConA (0.25 mg/ml) and IL-2 (12.5 ng/ml) were added to the wells. Drug was added at various doses two hours prior to activation with ConA and IL-2. The cells were incubated for 4 days at 37° C. On day 4, the cells were pulsed with tritiated thymidine and allowed to incubate for an additional 4 hours. Harvested cells were analyzed for incorporated tritiated thymidine, determined using a liquid scintillation counter. Dose response curves were prepared from the assay results and used to calculate an IC50 value for each compound tested.

Figure 2:
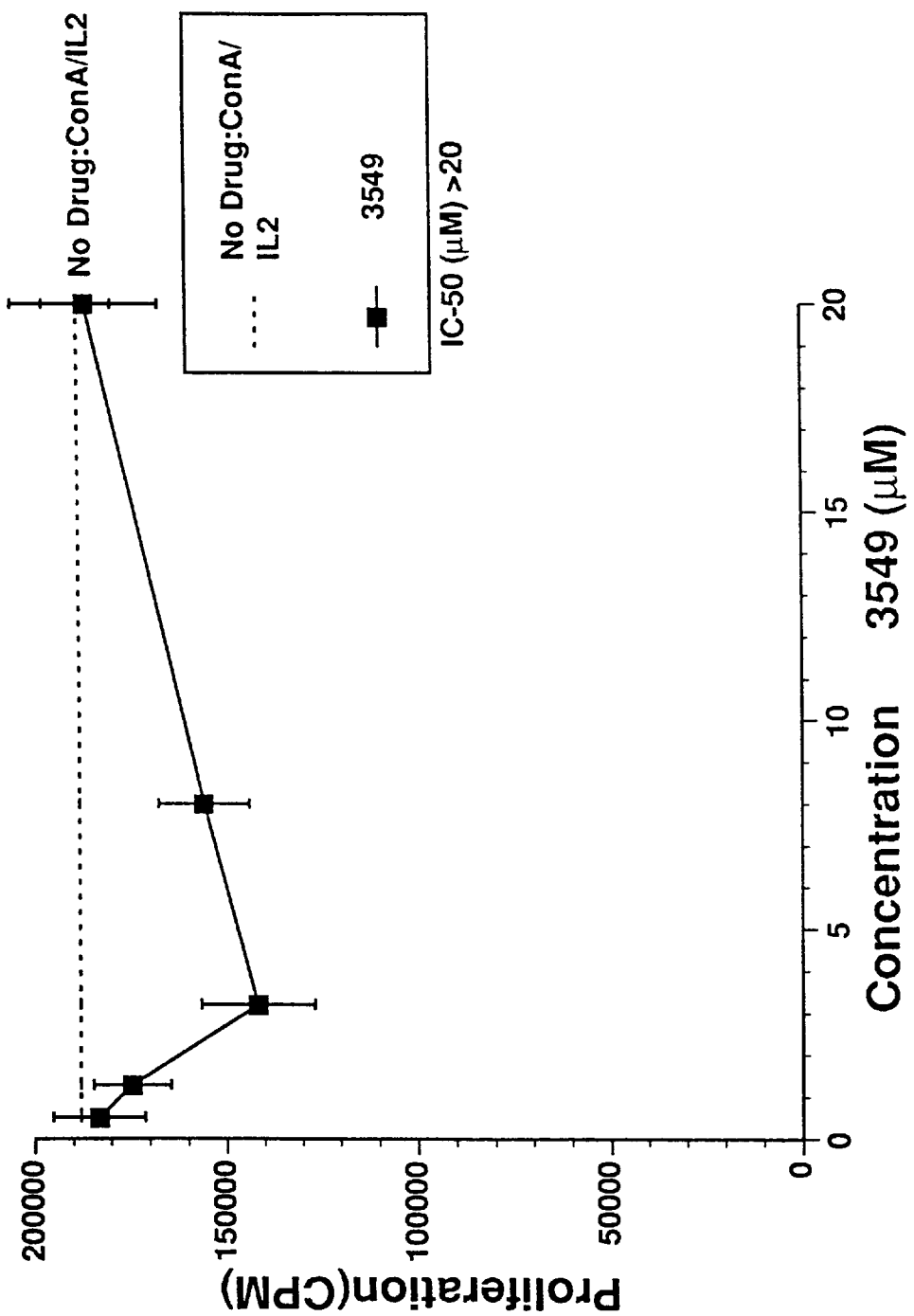

In representative dose response curves prepared for assays investigating compounds nos. 3546 and 3549, FIGS. 1 and 2, respectively, illustrate the inhibitive effects of these compounds on proliferation of thymocytes stimulated with ConA and IL-2. Background counts, without addition of representative inventive compounds were about 190 cpm. FIG. 1 illustrates a remarkable ability of inventive compound no. 3546 to inhibit proliferation of thymocytes in this system. FIG. 2 illustrates a less pronounced ability of the inventive compounds to inhibit thymocyte proliferation, suggesting specificity of particular inventive compounds for treating specific diseases. As shown, inventive compound no. 3546 inhibited ConA/IL-2 stimulated proliferation at compound concentrations less than 20 $\mu$M, with an IC50 value, experimentally calculated from this dose response curve, of about 4.8 $\mu$M. These concentrations plotted are within concentrations known to be achieved in vitro for treating disease.

EXAMPLE 14

This example illustrates an ability of inventive compounds nos. 1514 and 1583 to inhibit proliferation of peripheral blood mononuclear cells (PBMC) in response to allogeneic stimulation. This in vitro mixed lymphocyte reaction (MLR) assay is useful in assessing biological activity of an inventive compound. Procedurally, PBMC were obtained by drawing whole blood from healthy volunteers in a heparinized container, the whole blood samples diluted with an equal volume of hanks balanced salt solution (HBSS).

This mixture was layered on a sucrose density gradient, such as a Ficoll-Hypaque® gradient (specific gravity 1.08), and centrifuged (1000×g) for 25 minutes at no warmer than room temperature. PBMC were obtained from a band at a plasma-Ficoll interface, separated and washed at least twice in a saline solution, such as HBSS. Contaminating red cells are lysed, for example, by ACK lysis for 10 minutes at 37° C., and the PBMC were washed twice in HBSS. The pellet of purified PBMC was resuspended in complete medium, such as RPMI 1640 plus 20% human inactivated serum.

Proliferative response of PBMC to allogeneic stimulation was determined in a two-way MLR performed in a 96-well microtiter plate. Approximately $10^5$ test-purified PBMC in 200 $\mu$l complete medium were co-cultured with approximately $10^5$ autologous (control culture) or allogeneic (stimulated culture) PBMC. Allogeneic cells were from HLA disparate individuals. Varying doses of compounds nos. 1514 and 1583 were added simultaneously upon addition of cells to the microtiter plate. The cultures were incubated for 6 days at 37° C. in a 5% $CO_2$ atmosphere, after which time, tritiated thymidine was added (for example, 1 $\mu$Ci/well of 40 to 60 Ci/mmole) and proliferative inhibition was assessed by determining amount of tritiated thymidine taken up, using liquid scintillation counting.

Figure 3:
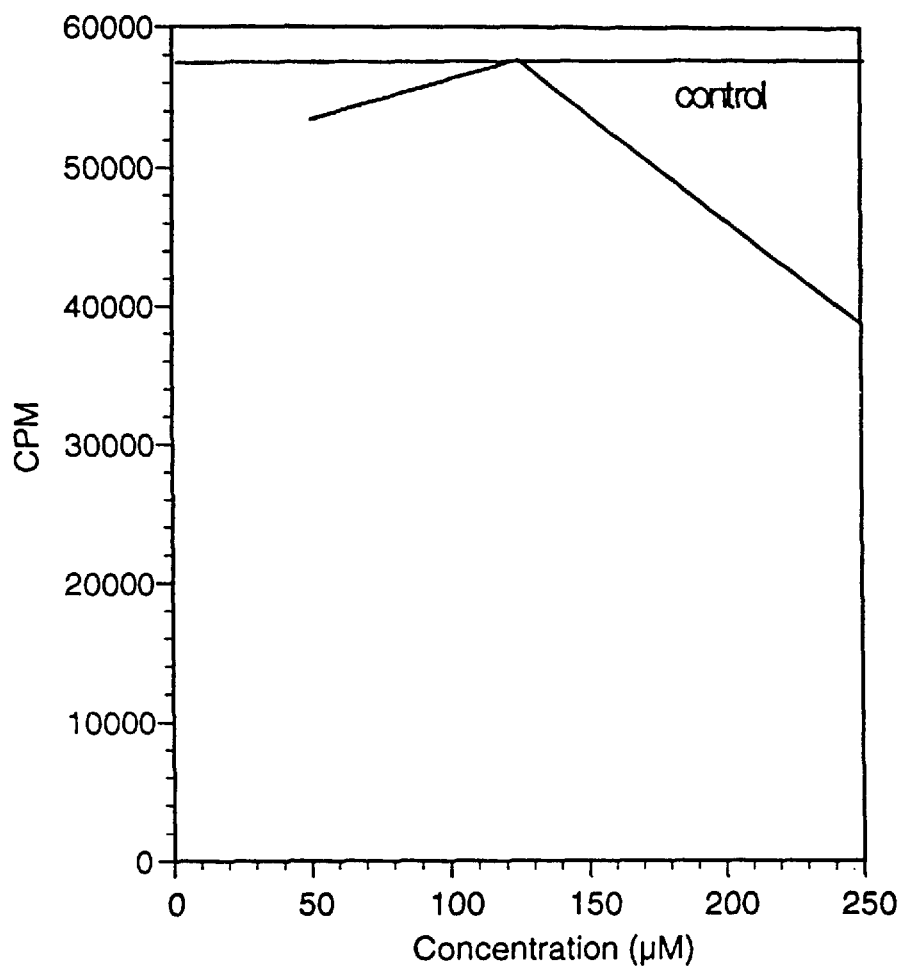
FIGS. 3 and 4 are plotted graphs of compound concentrations ($\mu$M) versus inhibition (as a function of incorporated thymidine, cpm) for compounds nos. 1514 and 1583, respectively, in a mixed lymphocyte reaction (MLR) assay.
Figure 4:
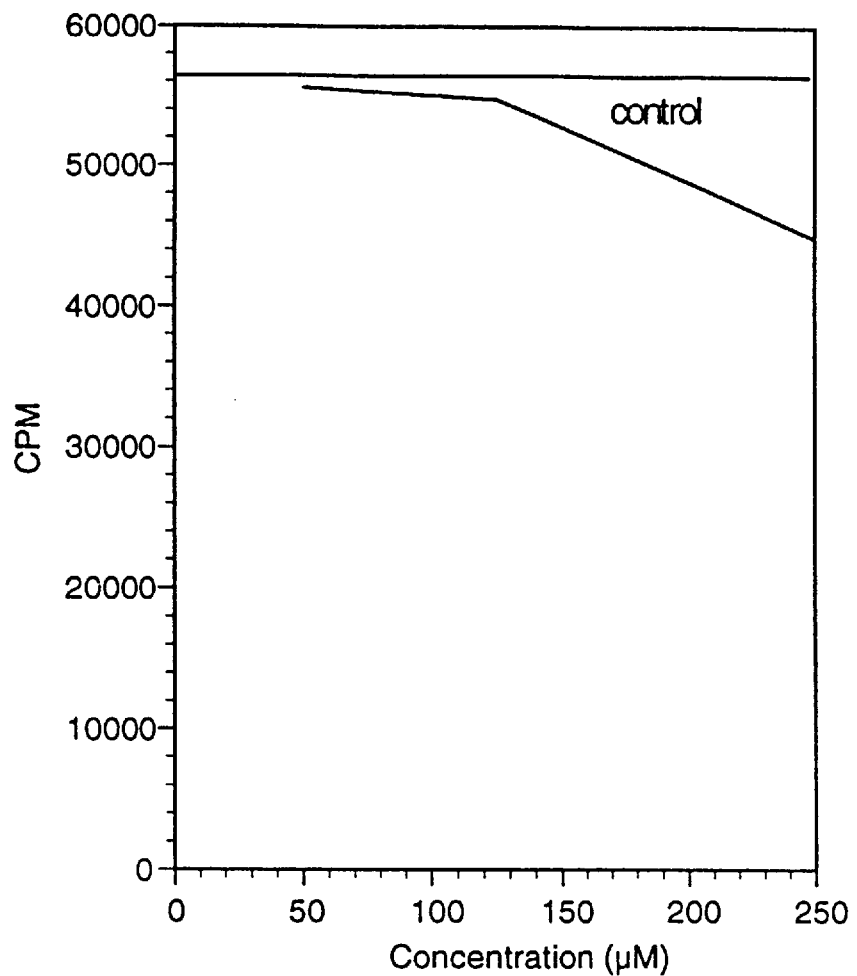

FIGS. 3 and 4 are plotted graphs of compound concentrations ($\mu$M) versus inhibition (as a function of incorporated thymidine, cpm) for compounds nos. 1514 and 1583, respectively. FIGS. 3 and 4 illustrate an ability of the inventive compounds tested to inhibit PBMC proliferation. At concentrations less than 250 $\mu$M, compound no. 1583 more significantly inhibited incorporation of thymidine. Similarly, although to lesser degrees in comparison to compound no. 1583, compound no. 1514 inhibited proliferation in this MLR assay at compound concentrations less than 250 $\mu$M.

EXAMPLE 15

This example illustrates inhibitive effects of the inventive compounds on Balb/3T3 cell proliferation in response to platelet derived growth factor (PDGF) stimulation.

Disregulated PDGF-proliferative response has been linked to a variety of diseases, including, e.g., restenosis, atherosclerosis, fibrosis, and tumor cell angiogenesis. Balb3T3 cells respond vigorously to PDGF stimulation, and are useful in vitro models for further study of PDGF-induced proliferation. In an assay useful in determining whether a compound would be useful in treating diseases characterized by this or similar disregulated proliferative responses, research indicates that many of the inventive compounds inhibit PDGF-induced proliferation of Balb/3T3 cells.

Balb/3T3 cells were plated in low serum-containing medium for 24 hours prior to stimulation with various concentrations of inventive compound. Specifically, in this assay, inventive compounds nos. 1529, 2538, 3537, 3542, 3546, 3554, 3557, 3559, 3562, 3564, 3571, 3573 and 3577 were tested. PDGF was added at varying concentrations along with tritiated thymidine. The cells were allowed to incubate for one day, following addition of PDGF and thymidine. 24 hours later, the cells were harvested and counted by liquid scintillation counting. Data obtained for each compound were plotted as % inhibition versus concentration of inventive compound and IC50 values experimentally calculated from the results plotted.

In conjunction with the Balb/3t3 proliferation assay, a related viability assay was conducted to assess the cytotoxicity of compounds which inhibit proliferation in this system. The assay protocol was identical to that performed above except that tritiated thymidine was not added after the 24 hour incubation with PDGF. Subsequent to incubation, a 10 μM solution of 2,7-bis-(2-carboxyethyl)-5(and-6)carboxyfluorescein, acetoxymethyl ester (BCECF—a compound that when cleaved by esterases, yields a fluorescent product, thus providing a measure of cell number) was added and the cells incubated for 30 minutes at 37° C. Following this incubation, BCECF was replaced with PBS and the plate read for fluorescence in a Millipore "cytofluor". Data obtained were plotted as a percent of control versus concentration of inventive compound tested and fifty percent (50%) lethal dose concentrations (LD50) for the inventive compounds tested were experimentally calculated from the plotted data.

Figure 5:
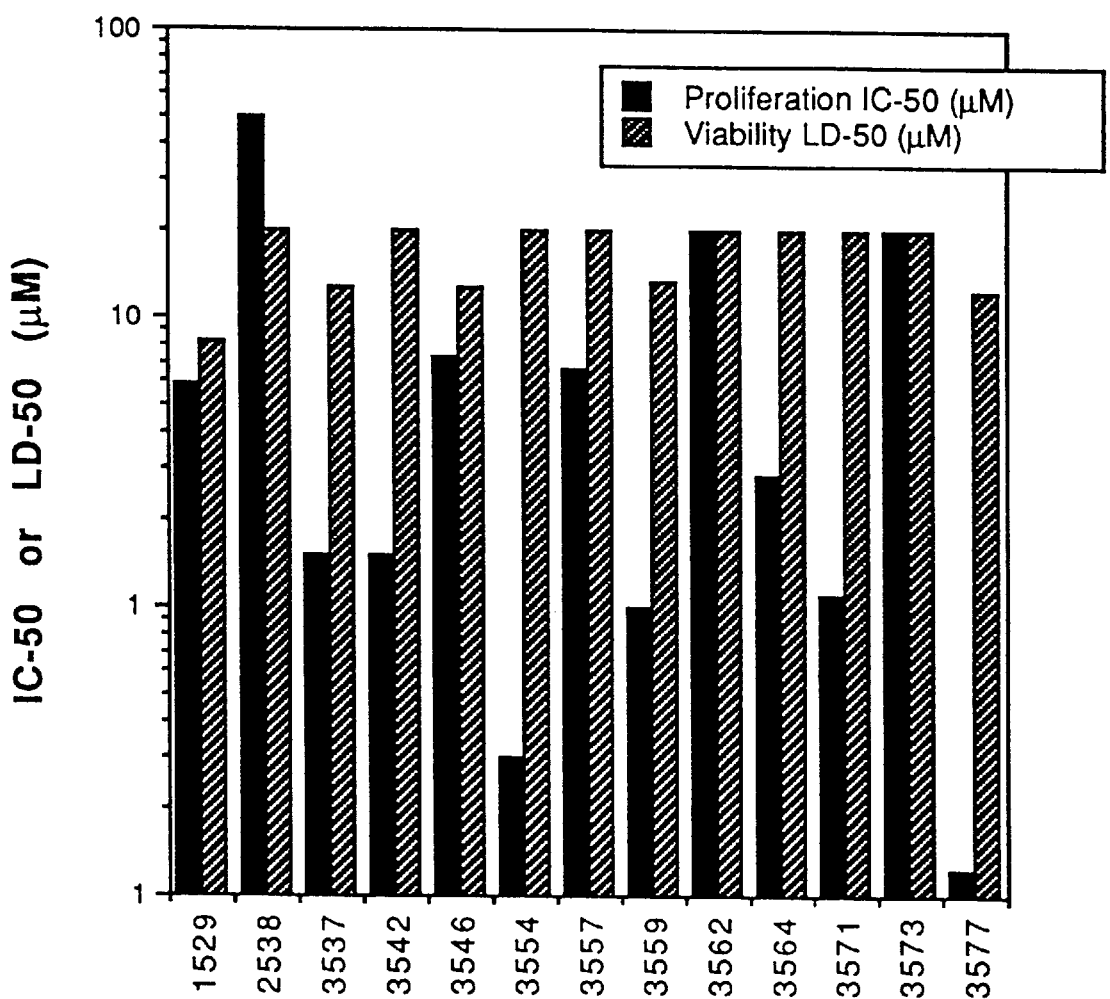
FIG. 5 reports the experimentally calculated IC50 values obtained in the an assay investigating inhibitive effects of various inventive compounds on proliferation of Balb/3T3 cells in response to stimulation by PDGF. In addition, FIG. 5 reports LD50 values for each inventive compound tested in the proliferation assay. The reported LD50 values were obtained in a corresponding viability assay.

FIG. 5 reports the experimentally calculated IC50 values obtained in the foregoing proliferation assay and LD50 values obtained in the corresponding viability assay for each inventive compound tested. The reported results indicate that many of the inventive compounds have IC50 values—the concentration of inventive compound in the proliferation assay inhibiting 50% proliferation of a control level—less than 10 μM. Specifically, inventive compounds nos. 3554, 3559, 3571 and 3577 have IC50 values at or below 1 μM. Of significance, compound no. 3577 inhibits 50% proliferation at an extremely low concentration of 0.1 μM!

LD50 values reported in viability assays for the inventive compounds tested indicate that many of the compounds have LD50 values above measurable levels. In FIG. 5, experimentally calculated IC50 values which equaled or exceeded 20 μM were reported as 20 μM. For a majority of compounds tested, a significant concentration interval exists between the IC50 and LD50 experimentally calculated, indicating that the inventive compounds are not only candidates for treating or preventing restenosis, atherosclerosis, fibrosis, tumor cell angiogenesis and other similar diseases, but possess significant windows for therapeutic treatment.

What is claimed is:

1. A therapeutic compound, including resolved enantiomers, diastereomers, hydrates, salts, or solvates thereof, having the formula:

$$\text{CORE MOIETY—(R)}_j$$

wherein:

j is an integer from one to three;

the core moiety is a pyrimidinyl moiety; and

R is selected from among hydrogen, hydroxyl, amino, substituted or unsubstituted $C_{(1-10)}$ alkyl, $C_{(2-10)}$ alkenyl, carbocyclic or heterocyclic groups and at least one R having formula I:

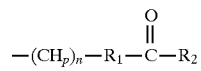

wherein:

p is two;

n is an integer from eight to twenty;

$(CH_p)_n$ is unsubstituted or substituted by one or more members selected from the group consisting of halogen, hydroxyl, and substituted or unsubstituted $C_{(1-10)}$ alkyl, $C_{(2-10)}$ alkenyl, $C_{(1-10)}$ alkoxyl, $C_{(1-10)}$ alkanoyloxyl, $C_{(1-10)}$ oxoalkyl, carbocyclic group and heterocyclic group;

$R_1$ is a member selected from the group consisting of O; substituted and unsubstituted $CH_2$, with the proviso that the $CH_2$ is not substituted with OH or $-OC_{(1-3)}$; $NR_3$, $R_3$ being hydrogen, substituted or unsubstituted $C_{(1-20)}$ alkyl, $C_{(5-20)}$ alkoxyl, $C_{(2-20)}$ alkenyl, $C_{(1-20)}$ hydroxyalkyl, or carbocyclic or heterocyclic group; $-C(R_4)_rO-$, r being one or two, $R_4$ being =O, hydrogen, substituted or unsubstituted $C_{(1-20)}$ alykl, $C_{(1-20)}$ alkoxyl, $C_{(2-20)}$ alkenyl, $C_{(1-20)}$ hydroxyalkyl, $C_{(1-20)}$ aminoalkyl, with the proviso that r is one when $R_4$ is =O;

$R_2$ is a member selected from the group consisting of substituted or unsubstituted $C_{(1-10)}$ alkyl, $C_{(1-10)}$ alkoxyl, $C_{(2-10)}$ alkenyl, $C_{(1-10)}$ hydroxyalkyl, or $C_{(1-20)}$ aminoalkyl; and wherein said carbocyclic or heterocyclic group is selected from the group consisting of; anthracenyl, bicyclo[4,4,0]decanyl, bicyclo[2,2,1]heptanyl, bicyclo[3,2,0] heptanyl, bicyclo[4,1,0]heptanyl, bicylo[2,2,1]hexanyl, bicyclo[4,3,0]nonanyl, bicyclo[2,2,2]octanyl, biphenyl, cyclopentadienyl, cyclopentanyl, cyclobutanyl, cyclobutenyl, cycloheptanyl, cyclohexanyl, cyclooctanyl, cyclopropanyl, 1,2-diphenylethanyl, indenyl, phenyl, terphenyl, napthalenyl, phenanthrenyl, toluenyl, xylenyl, benzofuranyl, benzothiophenyl, carbazolyl, furanyl, indolyl, oxazolyl, pyrrolidinyl, pyranyl, pyrrolyl, tetrahydrofuranyl, tetrahydropyranyl, tetrahydrothiophenyl and thiophenyl.

2. The compound according to claim 1, wherein j is one.

3. The compound according to claim 1, wherein the pyrimidinyl corresponds to formula II:

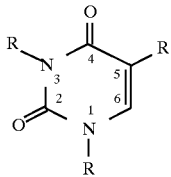

4. The compound according to claim 1, wherein the core moiety is a member selected from the group consisting of thyminyl and uracilyl.

5. A pharmaceutical composition comprising an effective amount of the compound defined in claim 1 and a suitable carrier, diluent or excipient.

6. The pharmaceutical composition of claim 5, wherein the composition is formulated for parenteral, topical or oral administration or for inhalation.

* * * * *

UNITED STATES PATENT AND TRADEMARK OFFICE
CERTIFICATE OF CORRECTION

PATENT NO. : 5,807,862
DATED : September 15, 1998
INVENTOR(S) : J. Peter KLEIN et al.

It is certified that error appears in the above-identified patent and that said Letters Patent is hereby corrected as shown below:

Claim 1

```
line 46 change "alykl" to --alkyl--.
line 47 after "hydroxyalkyl" insert --or--.
line 56 change "[4,4,0]" to --[4.4.0]--.
line 57 change "[2,2,1]" to --[2.2.1]--.
line 57 change "[3,2,0]" to --[3.2.0]--.
line 58 change "[4,1,0]" to --[4.1.0]--.
line 58 change "[2,2,1]" to --[2.2.1]--.
line 59 change "[4,3,0]" to --[4.3.0]--.
line 59 change "[2,2,2]" to --[2.2.2]--.
```

Signed and Sealed this

Second Day of February, 1999

Attest:

Attesting Officer

*Acting Commissioner of Patents and Trademarks*